(12) United States Patent
Wolf

(10) Patent No.: US 8,211,158 B2
(45) Date of Patent: Jul. 3, 2012

(54) BRANCH STENT GRAFT FOR AORTIC ANEURYSM REPAIR

(75) Inventor: Yehuda G. Wolf, Mevasseret Zion (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 235 days.

(21) Appl. No.: 12/515,752

(22) PCT Filed: Nov. 19, 2007

(86) PCT No.: PCT/IL2007/001428
§ 371 (c)(1),
(2), (4) Date: May 21, 2009

(87) PCT Pub. No.: WO2008/062405
PCT Pub. Date: May 29, 2008

(65) Prior Publication Data
US 2010/0057096 A1    Mar. 4, 2010

Related U.S. Application Data

(60) Provisional application No. 60/924,473, filed on May 16, 2007, provisional application No. 60/866,614, filed on Nov. 21, 2006.

(51) Int. Cl.
*A61F 2/06* (2006.01)
(52) U.S. Cl. ...................................... 623/1.11; 623/903
(58) Field of Classification Search .................. 128/898; 604/8–9; 606/108, 191, 194, 195, 200; 623/1.11–1.15, 1.23, 1.36, 1.16, 1.35
See application file for complete search history.

(56) References Cited

U.S. PATENT DOCUMENTS 4,712,551 A * 12/1987 Rayhanabad ..................... 604/8
(Continued)

FOREIGN PATENT DOCUMENTS
WO    WO 2008/062405    5/2008

OTHER PUBLICATIONS

International Preliminary Report on Patentability Dated Jun. 4, 2009 From the International Bureau of WIPO Re.: Application No. PCT/IL2007/001428.

(Continued)

*Primary Examiner* — Ryan Severson
*Assistant Examiner* — Ashley Cronin

(57) ABSTRACT

Described is a method for deploying a stent-graft in the aorta, the method including positioning a shunt to go along a portion of a brain-supplying artery (BSA) into the aorta; deploying a stent-graft in the aorta along a portion of the shunt; and removing the shunt. Also described is a removable shunt adapted for deployment along a brain-supplying artery into an aorta to supply blood to the artery during deployment of a stent-graft in the aorta, the removable shunt including a stiff segment that is stiff enough to remain at least partially open when between the aorta and the stent-graft and large enough to allow sufficient blood supply to the brain during the deployment of the stent-graft; and a mechanism for facilitating safe removal of the shunt from between the stent-graft and the aorta. Also described is a method of deploying a branch stent graft having a flaring portion in a blood vessel branching at a bifurcation from an aorta to connect to an aortic stent graft deployed in the aorta across the bifurcation, a branch stent-graft useful in the method, and a delivery system useful in the method.

18 Claims, 37 Drawing Sheets

U.S. PATENT DOCUMENTS

| | | | | |
|---|---|---|---|---|
| 5,383,854 | A | * | 1/1995 | Safar et al. ............... 604/98.01 |
| 5,709,713 | A | * | 1/1998 | Evans et al. ............... 623/1.53 |
| 6,139,517 | A | * | 10/2000 | Macoviak et al. ............. 604/8 |
| 6,293,964 | B1 | | 9/2001 | Yadav |
| 6,361,545 | B1 | * | 3/2002 | Macoviak et al. ............ 606/200 |
| 6,395,014 | B1 | * | 5/2002 | Macoviak et al. ............ 606/200 |
| 6,508,777 | B1 | * | 1/2003 | Macoviak et al. ........... 604/4.01 |
| 6,582,388 | B1 | * | 6/2003 | Coleman et al. .............. 604/8 |
| 6,673,040 | B1 | * | 1/2004 | Samson et al. ........... 604/101.01 |
| 2002/0010411 | A1 | | 1/2002 | Macoviak et al. |
| 2002/0115942 | A1 | * | 8/2002 | Stanford et al. .............. 600/562 |
| 2004/0006299 | A1 | * | 1/2004 | Barbut ...................... 604/8 |
| 2004/0147939 | A1 | * | 7/2004 | Rabkin et al. ............... 606/108 |
| 2005/0102018 | A1 | | 5/2005 | Carpenter et al. |
| 2006/0106455 | A1 | | 5/2006 | Furst et al. |
| 2006/0155358 | A1 | * | 7/2006 | LaDuca et al. ............... 623/1.11 |
| 2006/0155366 | A1 | * | 7/2006 | LaDuca et al. ............... 623/1.23 |
| 2007/0173921 | A1 | | 7/2007 | Wholey et al. |

OTHER PUBLICATIONS

International Search Report Dated Jul. 7, 2008 From the International Searching Authority Re.: Application No. PCT/IL2007/001428.
Written Opinion Dated Jul. 7, 2008 From the International Searching Authority Re.: Application No. PCT/IL2007/001428.
Office Action Dated Mar. 15, 2011 From the Israel Patent Office Re. Application No. 198862 and its Translation Into English.

* cited by examiner

BRANCH STENT GRAFT FOR AORTIC ANEURYSM REPAIR

RELATED APPLICATIONS

This Application is a National Phase of PCT Patent Application No. PCT/IL2007/001428 having International filing date of Nov. 19, 2007, which claims the benefit of U.S. Provisional Patent Application Nos. 60/924,473 filed on May 16, 2007 and 60/866,614 filed on Nov. 21, 2006. The contents of the above Applications are all incorporated herein by reference.

FIELD OF THE INVENTION

The invention is in the field of stent graft design and deployment.

BACKGROUND OF THE INVENTION

Thoracic aortic aneurysms (local dilatation of the artery which is prone to rupture) and dissections (splitting within the arterial wall prone to rupture, branch occlusion and aneurysmal degeneration) occur at a prevalence rate of 6/100,000 and 3/100,000 respectively and without treatment are associated with a high mortality rate which, in some situations, exceeds 50%.

Endovascular repair of aortic aneurysms, both thoracic and abdominal, is now an accepted and often preferred modality associated with a lesser mortality rate and complications compared to open surgical repair.

A large proportion of thoracic aneurysms and dissections involve the ascending aorta and the aortic arch. In these cases, endovascular repair with standard tubular stent-grafts is impossible because the three great vessels arising from the aortic arch (innominate or brachiocephalic artery, left common carotid artery and left subclavian artery), supplying the brain and the upper body, would be occluded. Occlusion of these arteries beyond several minutes can lead to severe complications and death. The current therapeutic alternative is open surgical repair, which in the case of ascending aorta and aortic arch aneurysms and dissections is extremely hazardous, may require total circulatory arrest (complete cessation of blood flow) and is associated with significant mortality exceeding 15-20%.

When a stent-graft is deployed in the aortic arch, it covers arteries that supply the brain. Therefore, it is important that such a stent-graft will have openings that face the brain supplying arteries (BSAs), and often the repair may require that the stent-graft have side-branches going into the brain-supplying arteries. Such openings and/or side branches may be prepared in advance, before the stent-graft is deployed (See, for instance, WO 02/076346, the disclosure of which is incorporated herein by reference), or in situ, when the stent-graft is already at the aorta. Aligning pre-made openings with the patient's BSAs may be difficult and occluding the brain-supplying arteries for a period long enough to allow in-situ preparation of such openings might cause severe brain damage or even death. Additionally, as the location of the BSAs is different in different individuals, a stent-graft with pre-made openings must be prepared for each patient individually, according to his own measures.

To prevent leakage of blood from between a branch stent graft and a main stent graft, the main stent graft may be made with one or more tubular sleeves extending outward from the fenestration. While this solution is customary for bifurcated abdominal aortic stent grafts at the aortic bifurcation, at other sites with greater anatomic variability, or where the space around the stent graft limits maneuvering, this solution is more complex.

A paper titled "In Situ Stent-Graft Fenestration to Preserve the Left Subclavian Artery" authored by Richard G. McWilliams; Micheal Murphy; David Hartley; Michael M.D. Lawrence-Brown; and Peter L. Harris, describes in-situ fenestration of a stent-graft deployed in the aorta while occluding the subclavian artery. However, occluding the left common carotid or innominate artery for the long time required for in-situ fenestration might cause severe damage to the patient.

The article "Modular branched stent-graft for endovascular repair of aortic arch aneurysm and dissection, by Timothy A. M. Chuter et al., published in J. vasc. Surg. 2003; 38:859-63 describes a bifurcated stent-graft inserted from the right carotid artery and extended from there into the ascending aorta. In this publication, two branches are revascularized by surgical bypass and not by stent-graft branches and no shunt was used.

SUMMARY OF THE INVENTION

An aspect of some embodiments of the invention relates to deploying a stent-graft in the aorta. In accordance with this aspect, a removable shunt is positioned to run alongside the deployed aortic stent-graft to shunt blood from the aorta to a brain-supplying artery, then the stent-graft is deployed pressing the shunt against the aorta, and the shunt is removed from between the aorta and the stent-graft.

In an embodiment of the invention, the brain-supplying artery that is connected to the aorta through the removable shunt is also connected to a second brain-supplying artery. This way, when the two brain-supplying arteries are occluded by the deployed stent-graft, they are both fed by the removable shunt.

In an exemplary embodiment of the invention, a stent-graft with two side arms going into two brain-supplying arteries is deployed, while blood is supplied to the two arteries through the above-mentioned removable shunt, and through a carotid perfusion catheter connecting between the two arteries as to allow direct blood flow between them. In this embodiment, described in FIGS. 3-12, the removable shunt is inserted to a first artery in the neck area of the patient, and goes along the artery into the aorta. Then the carotid perfusion catheter is deployed to directly connect the two arteries, such that the shunt supplies blood to the two arteries: to the first—directly, and to the second—through the perfusion catheter (FIG. 5A). Then, the stent-graft is deployed, pressing the shunt against the aorta (FIG. 6). An opening is made with a fenestration instrument inserted through the second artery (FIG. 7), and a side-branch going from the aorta to the second artery is deployed (FIG. 8). The shunt is removed from between the aorta and the stent-graft (FIG. 9), and the first artery in now supplied with blood from the second artery through the perfusion catheter. The stent-graft is fenestrated with a fenestration instrument going through the first artery (FIG. 10), and a side-branch going from the aorta to the first artery is deployed (FIG. 11). Finally, the perfusion catheter is removed and all punctures in the arteries are sutured (FIG. 12).

An aspect of some embodiments of the invention relates to a removable shunt, designed to let through a sufficient blood supply to a brain-supplying artery, along which it runs into the aorta while being compressed between a stent-graft and the aorta. Optionally, the blood supply is sufficient also to feed another brain-supplying artery. For the shunt to supply sufficient blood when pressed, a portion of the shunt is stiff enough, so it remains at least partially open when compressed between the aorta and the stent-graft. In an exemplary embodiment of the invention, the diameter of the stiff enough portion of the shunt is large enough, so that it allows sufficient blood supply to the brain during the deployment of the stent-graft.

Preferably, the shunt as a whole is flexible enough to be inserted through the BSA and into the aorta in any angle that would be required for clinical purposes.

In an embodiment of the invention, the shunt is designed to allow its safe removal from between the stent-graft and the aorta.

Optionally, for facilitating safe removal of the shunt, the shunt has a low-friction outer surface, for example, the outer surface is smooth and hydrophilic, optionally made of Teflon. This way, when the shunt is pulled out from between the aorta and the stent-graft, it releases smoothly thanks to the low friction.

Additionally or alternatively, the shunt has one or more safe-removal facilitating mechanism. One such mechanism may be a sleeve going all around the body of the shunt from near its tip to the end of the stiff enough portion. In an exemplary embodiment, the sleeve has particularly low friction with the outer surface of the shunt body. Optionally, the sleeve is made to invert when the shunt is pulled out (See FIG. 16B), allowing smooth pulling of the shunt out of the sleeve, and then safe pulling of the sleeve out of the narrow space between the stent-graft and the aorta.

Additionally or alternatively, the shunt may have around it runners to facilitate its safe pulling out. The runners, optionally metallic, optionally from 4 to 6, run along and around the graft and are inserted with the shunt. A release mechanism releases the runners from the main body of the shunt, and optionally also from one another, so that the shunt may be removed while leaving the runners in place. This way the shunt is removed while there are still stationary rods around it. After removal of the shunt, the much thinner rod structure may be removed or, if the release mechanism released the rods (runners) from each other, they can be removed one by one.

Additionally or alternatively, the sleeve includes axial reinforcement wires, so if the sleeve tears apart, parts will stay held together by the wires.

Additionally or alternatively, the shunt is designed to include an introducer with a channel for a balloon, to be inflated to create space between the shunt and the deployed stent-graft, thereby facilitating the safe removal of the shunt from between the aorta and the stent-graft (See FIGS. 16C and 17).

An aspect of the invention concerns a method for releasing a shunt pressed against a graft, the method comprising inflating a balloon or other expandable structure as to create space between the shunt and the graft.

An aspect of some embodiments of the present invention is a kit with devices for deploying a stent-graft in the aorta. Such a kit includes a removable shunt as described above, and at least one additional device required for the deployment according to any embodiment of the invention. The additional device may be the fenestration instrument used for creating an opening in the stent-graft when deploying a side-branch to the stent-graft; one or more carotid perfusion catheters for shunting blood between the two brain-supplying arteries (BSA) through openings made in the neck area of the patient as described above, a branched connector, sized for connecting between the perfusion catheter and the removable shunt when deployed in the neck area of the patient; or an introducer, for introducing a balloon through the removable shunt to facilitate its removal.

An aspect of some embodiments of the present invention relates to a branch stent graft capable of achieving a reliable seal with an aortic stent graft, such that when deployed together with the aortic stent graft via a fenestration therein, blood does not leak between the aortic and the branch stent grafts. Preferably, a reliable seal is achievable even with a simple fenestration, without a leak preventing sleeve.

In one embodiment of the invention, a branch stent graft is made with a flaring end that in deployment is flared inside the aortic stent graft and seals to it. Preferably, the flaring end is made with fabric, configured for apposition against fabric of the aortic stent graft to improve the seal.

Some embodiments of the invention provide for different ways of achieving a reliable seal.

In an embodiment of the invention, reliability of the seal is increased, by providing an expanding stent-portion, for expanding the flaring end of the branch graft so that the flaring end is kept flat and fixed and does not flap with blood flow inside the aorta.

In an embodiment of the invention, reliability of the seal is increased by providing stabilizing wires going from the vicinity of the flaring end. The stabilizing wires are designed to press against the wall of the aortic stent graft opposite to the fenestration, in order to fix the flared portion of the branch stent graft against the luminal surface of the aortic stent graft in the area surrounding the fenestration. The luminal surface is the surface that defines a lumen in the stent graft.

In an embodiment of the invention, reliability of the seal is increased by providing an inflatable cuff located distal to the flared portion so that it is inflated outside the aortic stent graft while the flared portion is inside it. Optionally, an additional inflatable cuff is placed sufficiently close to the first, so that when inflated the two cuffs press against each other with the fabric of the aortic stent graft compressed between them as to further improve the seal.

In an embodiment of the invention, the flared portion is a part of the inflatable cuff deployed inside the aortic stent graft.

An aspect of some embodiment of the invention relates to deploying a branch stent graft having a flared portion and a tubular portion to connect to an aortic stent graft at the flaring portion, by starting deployment of the flaring portion before starting deployment of the tubular portion.

Preferably, the flaring portion is first attached to the aortic stent graft at the vicinity of the fenestration, and only then begins the deployment of the tubular portion. This is especially advantageous in embodiments where after the tubular portion is deployed it is difficult to change its position and orientation, to improve the seal between the flared portion and the aortic stent graft.

In an embodiment of the invention, the branch stent graft is connected to a fully deployed aortic stent graft. Alternatively, the aortic stent graft is fenestrated and the branch stent graft is inserted through the fenestration when the aortic stent graft is only partially expanded in the radial direction, and the radial expansion continues after the flaring portion of the branch stent graft apposes the fenestration.

In an embodiment of the invention, the aortic stent graft is fenestrated in situ with a fenestration tool guided on a guide-wire through a blood vessel branching from the aortic arch. After an opening is made, the fenestration tool is taken out, and the branch stent graft is deployed through the same blood vessel and on the same guide-wire, thus allowing easier finding of the fenestration point.

Optionally, before the branch stent graft is delivered through the fenestration, the fenestration is widened by inflating inside it a balloon.

Optionally, after the branch stent graft is delivered through the fenestration, its proximal portion is expanded inside the aortic stent graft, and the expanded proximal portion is pulled back to attach to the luminal surface of the aortic stent graft.

Optionally, the branch stent graft is secured to the delivery system as to prevent non-intentional release of the stent graft from the delivery system during pulling. Accordingly, an aspect of some embodiments of the invention concern a stent graft secured to a delivery system as to prevent releasing of the stent graft from the delivery system upon pulling.

An aspect of some embodiments of the invention concerns a method of deploying an aortic stent graft in the aortic arch, and a branch stent graft in a blood supplying artery branching from the aortic arch. The method comprises inserting into the aorta an expandable aortic stent graft; only partially expanding the aortic stent graft, inserting the branch stent graft to a fenestration in the partially expanded aortic stent graft; and further expanding the aortic stent graft, optionally to its final dimensions.

In an embodiment of the invention, the expandable aortic stent graft is made with a fenestration ready to receive the branch stent graft. Optionally, such a fenestration has a leek preventing sleeve as described above.

Optionally, the method also comprises making a fenestration in situ. This option may be especially desirable in case the fully expanded aortic stent graft covers more than one brain supplying artery.

There is thus provided, according to an exemplary embodiment of the invention, a method for deploying a stent-graft in the aorta, the method comprising
 (a) positioning a shunt to go along a portion of a brain-supplying artery (BSA) into the aorta;
 (b) deploying a stent-graft in the aorta along a portion of the shunt; and
 (c) removing the shunt.

In an embodiment of the invention, deploying the stent-graft comprises forming in the stent-graft an opening facing a BSA, and/or positioning a side-branch of the stent-graft in one or more of the BSAs, such that the side-branch is connected to the stent-graft at the vicinity of an opening in the stent-graft, the opening facing the BSA.

Optionally, the stent-graft comprises a side-branch, and positioning a side-branch of the stent-graft in a BSA comprises extending said side-branch into the BSA.

Optionally, positioning a side-branch in a BSA comprises preparing the side-branch in situ.

Optionally, positioning a side-branch in a BSA comprises insertion of a side-branch from a femoral artery through the stent-graft and an opening in the stent-graft, said opening facing said BSA.

In an exemplary embodiment, positioning a side-branch in a BSA comprises insertion of a side-branch from the BSA into an opening in the stent-graft, and dilating a portion of the side-branch to hold the stent-graft from the inside of the stent-graft.

In an embodiment of the invention, the method comprising holding the stent-graft in place to prevent its dislodging during removal of the shunt. Optionally, holding the stent-graft in place comprises inflating a balloon inside the stent-graft. Additionally or alternatively, holding the stent-graft in place comprises momentarily stopping the heart.

Optionally, the brain-supplying artery is one of the following: the left subclavian artery; the left common carotid artery, the right common carotid artery and the innominate artery.

In an embodiment of the invention, removing the shunt comprises expanding an expandable device, for example, a balloon, between the stent-graft and the aorta to facilitate release of the shunt.

In an embodiment of the invention, the shunt comprises a stiff segment and a sleeve going around and along the stiff segment, and removing the shunt comprises inverting the sleeve.

In an embodiment of the invention, the method includes connecting the brain-supplying artery to a second brain-supplying artery with a carotid perfusion catheter, such that if the passage between the aorta and the second brain-supplying artery is occluded, blood flows into the second brain-supplying artery through the carotid perfusion catheter. Optionally, such method comprises insertion of a fenestration instrument through the second BSA and forming an opening in the stent-graft, the opening facing the second BSA.

In an embodiment of the invention, after the shunt is removed from the brain-supplying artery a fenestration instrument is insertion through the brain-supplying artery and an opening is formed in the stent-graft, the opening facing the brain-supplying artery.

There is further provided by an exemplary embodiment of the invention a removable shunt adapted for deployment along a brain-supplying artery into an aorta to supply blood to the artery during deployment of a stent-graft in the aorta, the removable shunt comprising
 a stiff segment that is stiff enough to remain at least partially open when between the aorta and the stent-graft and large enough to allow sufficient blood supply to the brain during the deployment of the stent-graft, and
 a mechanism for facilitating safe removal of the shunt from between the stent-graft and the aorta.

Optionally, said mechanism includes an invertible sleeve. The invertible sleeve optionally includes reinforcement wires that run parallel to the stiff segment.

In an embodiment of the invention, the mechanism for facilitating safe removal of the shunt includes an introducer for a balloon to be inflated between the stent-graft and the aorta.

In an embodiment of the invention, the stiff segment of the removable shunt is capable of withstanding compressive force of 1 kg per cm length without deforming in more than 10%.

In an embodiment of the invention, the stiff segment has an outer diameter of 8 mm or less, optionally 5 mm or more.

Optionally, A removable shunt according to embodiments of the invention has a stiff segment of 15 cm length or more, optionally 30 cm length or less.

In an embodiment of the invention, the removable shunt includes a front segment that is moderately soft and deformable as not to injure the inside of the aorta, and not floppy, as not to fold or bend with the blood flow.

There is also provided according to an exemplary embodiment of the invention, a kit comprising a removable shunt according to any embodiment of the invention, and at least one additional device required for the deployment a stent-graft in accordance with an embodiment of the invention.

Optionally, said additional device is selected from a fenestration instrument for creating an opening in a stent-graft; a carotid perfusion catheter for shunting blood between two brain-supplying arteries (BSA) through openings made in a neck of a patient; a branched connector, sized for connecting between the perfusion catheter and the removable shunt, said connecting being in a neck of a patient; and an introducer, for introducing a balloon through the removable shunt to facilitate its removal from between the stent-graft and the aorta.

There is also provided by an exemplary embodiment of the invention, a method for releasing a temporary shunt pressed to a graft without dislodging the graft, the method comprising inflating a balloon to create space between the graft and the shunt as to release the shunt. Optionally, the balloon is introduced via the shunt.

In an embodiment of the invention, the method includes holding the graft in place, optionally with inflating a balloon inside the graft.

Optionally, the graft is a stent-graft deployed in an aorta, and the shunt is pressed to the graft by the aorta.

There is thus also provided, according to an exemplary embodiment of the invention, a method of deploying a branch stent graft having a flaring portion in a blood vessel branching at a bifurcation from an aorta to connect to an aortic stent graft deployed in the aorta across the bifurcation, the aortic stent graft having a luminal surface defining a luminal space, and an opening facing the blood vessel at the bifurcation, the method comprising:

(a) inserting at least a portion of the branch stent graft into the luminal space through the opening;
(b) expanding the flaring portion of the branch stent graft within the luminal space; and
(c) pulling the branch stent graft so as to appose the flaring portion against the luminal surface of the aortic stent graft.

According to yet another exemplary embodiment of the invention there is provided a method of deploying a branch stent graft having a tubular portion and a flared portion to connect to an aortic stent graft via the flaring portion, the method comprising first at least partially expanding the flaring portion; and thereafter expanding the tubular portion.

In an exemplary embodiment of the invention, the method comprising apposing the flaring portion against a luminal surface of the aortic stent graft so as to prevent leakage of blood between the flaring portion and the luminal surface. Optionally, expanding the tubular portion is performed after said apposing. Alternatively or additionally, expanding the flaring portion comprises inflating a cuff.

In an exemplary embodiment of the invention, the method comprising pressing the flaring portion against the luminal surface.

Optionally, pressing the flaring portion comprises expanding a flaring stent, such that when expanded, the stent presses a graft material of the flaring portion against a graft material of the aortic stent graft.

Optionally, the flaring stent is flaring from a tubular portion of the branch stent graft.

In an exemplary embodiment, pressing comprises inflating a balloon within the luminal space.

Alternatively or additionally, pressing comprises deploying wire stabilizers extending from the vicinity of the flaring portion to a portion of the luminal surface facing the opening in the aortic stent graft.

Alternatively or additionally, pressing comprises inflating a cuff outside the aortic stent graft and at the vicinity of the opening, as to press the aortic stent graft against the flaring portion of the branch stent graft.

In an exemplary embodiment of the invention, inserting is with a delivery system comprising a fixer, fixing the branch stent graft to the delivery system, and the method comprises disabling the fixer after the pulling.

Optionally, disabling the fixer comprises cutting a fixing suture.

Alternatively or additionally, disabling the fixer comprises releasing a fixing hook.

In an exemplary embodiment of the invention, the method comprising guiding a fenestration tool on a guide-wire through the blood vessel to the aortic stent graft, and creating the opening with said fenestration tool.

Optionally, the method further comprising taking the fenestration tool out of the blood vessel, and deploying the branch stent graft on said guide-wire.

Optionally, the method comprises widening the opening made by the fenestration tool, by inflating a balloon in the opening.

There is also provided according to an exemplary embodiment of the invention, a branch stent graft configured for attachment in a branched configuration to an aortic stent graft at an opening in a luminal surface defining a luminal space of the aortic stent graft, the branch stent graft comprising:

(a) an expandable tubular stent graft; and
(b) an expandable flaring graft at an end of the tubular stent graft, said expandable flaring graft being configured to physically closely fit the luminal surface of the aortic stent graft at the peri-fenestration area when the flaring graft is expanded.

In an exemplary embodiment, the expandable flaring graft is perpendicular to the tubular stent graft, when the expandable flaring graft is expanded.

Optionally, the expandable flaring graft is configured to convexly expand as to follow concaveness of the surface that defines the luminal space of the aortic stent graft.

In an exemplary embodiment of the invention, the tubular stent graft comprises a flaring stent portion configured to bias the flaring graft against the luminal surface of the aortic stent graft at the peri-fenestration area.

Optionally, the stent graft according to any of the above-described embodiments comprises an inflatable cuff configured to bias the flaring graft against the aortic stent graft at the peri-fenestration area.

Optionally, the inflatable cuff comprises the flaring graft.

In an exemplary embodiment of the invention, a branch stent graft comprises wires configured to expand from the end of the tubular stent graft to the luminal surface opposite the peri-fenestration area, so as to bias the flaring graft portion against the luminal surface of the aortic stent graft at the peri-fenestration area.

Optionally, the branch stent graft comprises an inflatable cuff located distal to the flared portion so that at deployment the cuff is inflated outside the aortic stent graft to press the aortic stent graft against the flaring graft.

Optionally, the branch stent graft a first inflatable cuff and a second inflated cuff, said second inflatable cuff being sufficiently close to the first, so that when the two cuffs are inflated, the two cuffs press against each other.

Optionally, the branch stent graft self-expandable.

Optionally, the branch stent graft is loaded at a front end of a delivery system with the flaring graft in front of the tubular stent graft.

There is also provided in accordance with an exemplary embodiment of the present invention a delivery system for intraluminally delivering a branch stent graft to connect to an aortic stent graft, the delivery system comprising:

a delivery sheath having a back end and a front end;
a branch stent graft having a tubular portion and a flaring portion,
a delivery sheath, sheathing the branch stent graft; and
a fixing mechanism, fixing the branch stent graft to the delivery system so as to prevent it from being inadvertently released from the sheath when the delivery sheath is pulled backwards.

Optionally, the fixing mechanism comprises attaching the branch stent graft to the delivery system.

In an exemplary embodiment, the delivery system comprises a self-expandable hook attaching the branch stent graft to the delivery system, such that releasing the hook from the delivery sheath releases the branch stent graft from the delivery system.

Optionally, the branch stent graft is loaded in the delivery sheath with the flaring portion in front of the tubular portion.

There is also provided, by an exemplary embodiment of the present invention, a method of deploying an aortic stent graft in the aortic arch, and a branch stent graft in a blood supplying artery branching from the aortic arch, the method comprising:

inserting into the aorta an expandable aortic stent graft;

only partially expanding the aortic stent graft, inserting a portion of the branch stent graft through a fenestration in the partially expanded aortic stent graft; and further expanding the aortic stent graft.

Optionally, the method comprises creating the fenestration when the aortic stent graft is inside the aorta.

Glossary

The following terms will be used throughout the description and claims and should be understood in accordance with the invention to mean as follows:

A stent—an expandable structure, usually made of a mesh of metal, plastic, or other flexible and biocompatible materials, used to hold blood vessels or grafts open. Optionally, a stent is balloon expandable, alternatively or additionally, a stent is self-expandable.

A graft—also known in the art as a prosthetic vascular graft, is a conduit or conduit portion, made of fabric such as polyester or PTFE, which is impervious to blood and when in the form of a tube can serve to convey blood from one point to another.

A stent graft—A vascular graft supported on at least one stent so that the graft retains its general form. Optionally, a graft of a stent graft is fixed by the at least one stent to a native vasculature.

Aortic stent graft (ASG)—is a stent graft configured for deployment in the aorta. For deployment in an area of the aorta that contains branches that are to be left open an aortic stent graft may be fenestrated before it is deployed in the aorta, or afterwards. Aortic stent grafts are usually inserted into the aorta from the common femoral artery in the groin. Non-limiting examples of aortic stent grafts that may be used in accordance with embodiments of the present invention include a standard, current-design, thoracic aortic stent grafts (which are usually tubular and of a large caliber) and standard current design abdominal stent grafts (which are usually bifurcated and of smaller caliber).

Branch stent graft (BSG)—a stent graft configured for insertion through a fenestration in an aortic stent graft into one of the arteries branching from the aorta (also referred to as branch arteries) at a bifurcation. In exemplary embodiments of the invention, a branch stent graft is configured to be inserted from the branch artery through the fenestration and into the aortic stent graft. In other exemplary embodiments of the invention, a branch stent graft is configured to be inserted from the aortic graft through the fenestration and into the branch artery.

Proximal—close to the heart.

Distal—further away from the heart.

Retrograde—opposite to the direction of arterial flow, i.e. from distal to proximal.

Antesgrade—with the direction of arterial flow, i.e. from proximal to distal.

Front end (of a device, for instance a delivery system or a stent graft)—the tip of the device, further away from the handle.

Back end (of a device)—an end away from the tip, closer to the handle.

Flared portion of a branch stent graft—a spread out portion of the branch stent graft (BSG), designed to be inside the aortic stent graft (ASG) and appose the luminal surface of the aortic stent graft.

Peri-fenestration area—an area on the luminal surface of the aortic stent graft (ASG) that surrounds a fenestration and is expected to appose (come in contact with) the ab-luminal surface of the flared portion of the branch stent graft, when the branch stent graft is deployed in the aortic stent graft.

BRIEF DESCRIPTION OF THE DRAWINGS

Non-limiting examples of embodiments of the present invention are described below with reference to figures attached hereto and listed below. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION OF EXEMPLARY EMBODIMENTS

In the following, first described are exemplary methods for deploying a stent-graft in the aorta according to some embodiments of the invention, then a deployment procedure according to an exemplary embodiment of the invention is described in detail, and then some devices useful in the exemplary deployment procedure are described.

Deployment Methods

Figure 1:
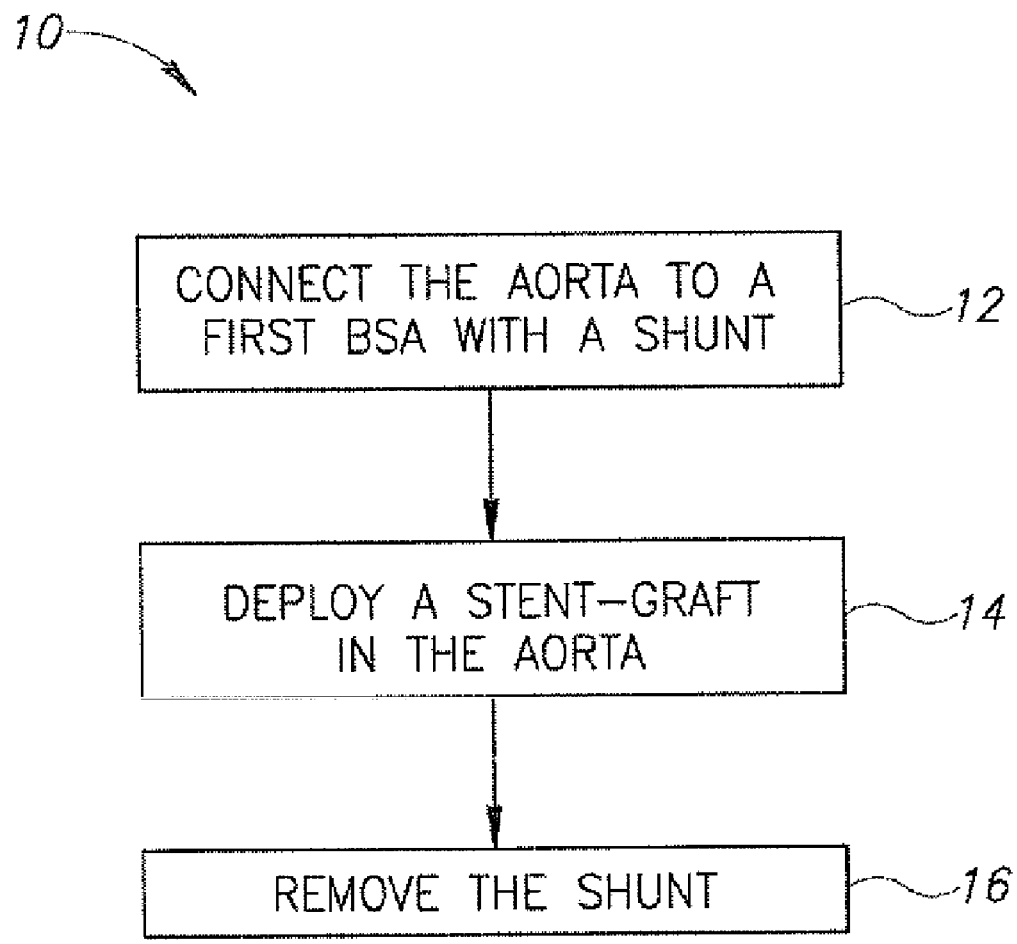
FIGS. 1 and 2 are flowcharts showing actions taken in two methods according to embodiments of the invention.

FIG. 1 is a flowchart of actions to be taken in accordance with a method (10) according to an exemplary embodiment of the present invention. The actions shown are described in FIGS. 3-12.

The method (10) comprises inserting (12) a removable shunt along a portion of the BSA into the aorta; deploying (14) a stent-graft in the aorta; and removing (16) the shunt.

Inserting (12) a shunt connecting the aorta and the first BSA is for allowing blood flow to the brain during deployment of the stent-graft, through the first BSA, which otherwise would be occluded by the stent-graft, at least until after the stent-graft is fenestrated, or a pre-made opening in the stent-graft is aligned with the BSA.

Deploying (14) the stent-graft in the aorta is the main purpose of the entire procedure. Care should be taken that apart of being deployed in a therapeutically effective location, the stent-graft is deployed without occluding the removable shunt that is responsible for supplying blood to the brain during deployment.

Optionally, deploying the stent-graft includes making openings in the stent-graft in positions facing the BSAs. Additionally or alternatively, the stent-graft has pre-made openings and deploying includes aligning them with the BSAs. In an embodiment of the invention, one opening is pre-made and aligned during deployment, and another is fenestrated during deployment from within a BSA. Optionally, two or more openings are fenestrated during deployment. As the shunt supplies blood to the brain, the physician has enough time to deploy the stent-graft without haste, and may allow the deployment and branch-creation process 5-15 minutes without having to fear he causes brain damage to the patient. If the patient's brain is cooled by 5-15° C., this period may be even longer, up to 30 minutes.

Similarly, deploying (14) may include constructing side-branches to the stent-graft, extending from the stent-graft into one or more of the BSAs. A side-branch, similarly to an opening, may be pre-made and extended during deployment, or may be inserted into the BSA before or after the stent-graft is positioned in the aorta. Constructing the side-branches may be carried out as described, for instance, in any one of WO 2005/046526 and WO 2005/027784 the disclosure of both of which is incorporated herein by reference.

Optionally, constructing a side arm comprises insertion of a side-branch from the BSA into an opening in the stent-graft, and dilating a portion of the side-branch to hold the stent-graft from the inside of the stent-graft.

Removing the shunt (16) can be tricky. As the shunt is pressed between the stent-graft and the inner wall of the aorta, removing the shunt might dislodge the stent-graft, that is, move the stent-graft to a position where it is less therapeutically effective, or not effective at all. As dislodging might have severe effects, up to causing death of the patient, the shunt is optionally designed to allow safe removal under most conceivable situations. Some embodiments of shunts with removal facilitating mechanisms are described in detail below.

Additionally or alternatively to using a shunt designed to be removed safely from between the graft and the aorta, it is possible to remove the shunt in a method comprising holding the stent-graft in place to prevent it from dislodging. In one embodiment, this is done by blowing up a large balloon, for instance, a gore trilobe balloon, within the stent-graft; supporting the stent-graft by maintaining position at the back end of the shaft of the balloon catheter from the groin; and inserting a relatively stiff introducer into the already formed fenestration or side arm in the innominate artery to give the main stent-graft some support. Optionally, the method also comprises stopping the heart briefly, for instance, with adenosine, or use a pacemaker for rapid pacing, to reduce the forces exerted on the graft by the blood flow.

Figure 2:
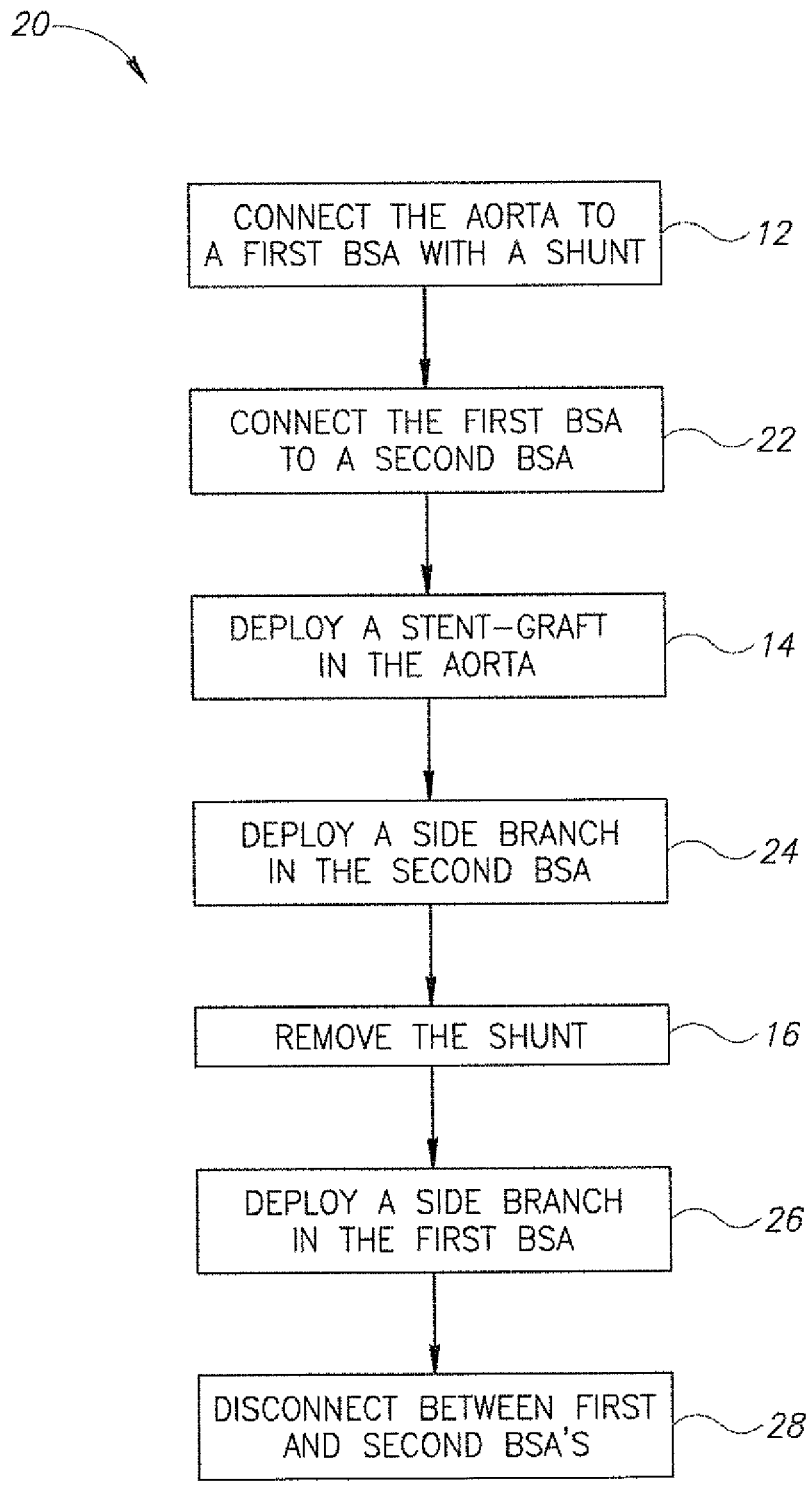

FIG. 2 is a flowchart of actions to be taken in accordance with a more specific method (20) according to an exemplary embodiment of the present invention.

In the exemplary embodiment depicted in FIG. 2, the method (20) includes inserting (12) the removable shunt; connecting (22) the first BSA and a second BSA; deploying the stent-graft (14), deploying (24) a stent-graft side-branch in the second BSA, removing the shunt (16); deploying (26) a stent-graft side-branch in the first BSA; and disconnecting the connection made between the two BSAs (28).

Of these actions, those numbered as 12, 14, and 16 were explained in reference to FIG. 1.

Figure 5A:
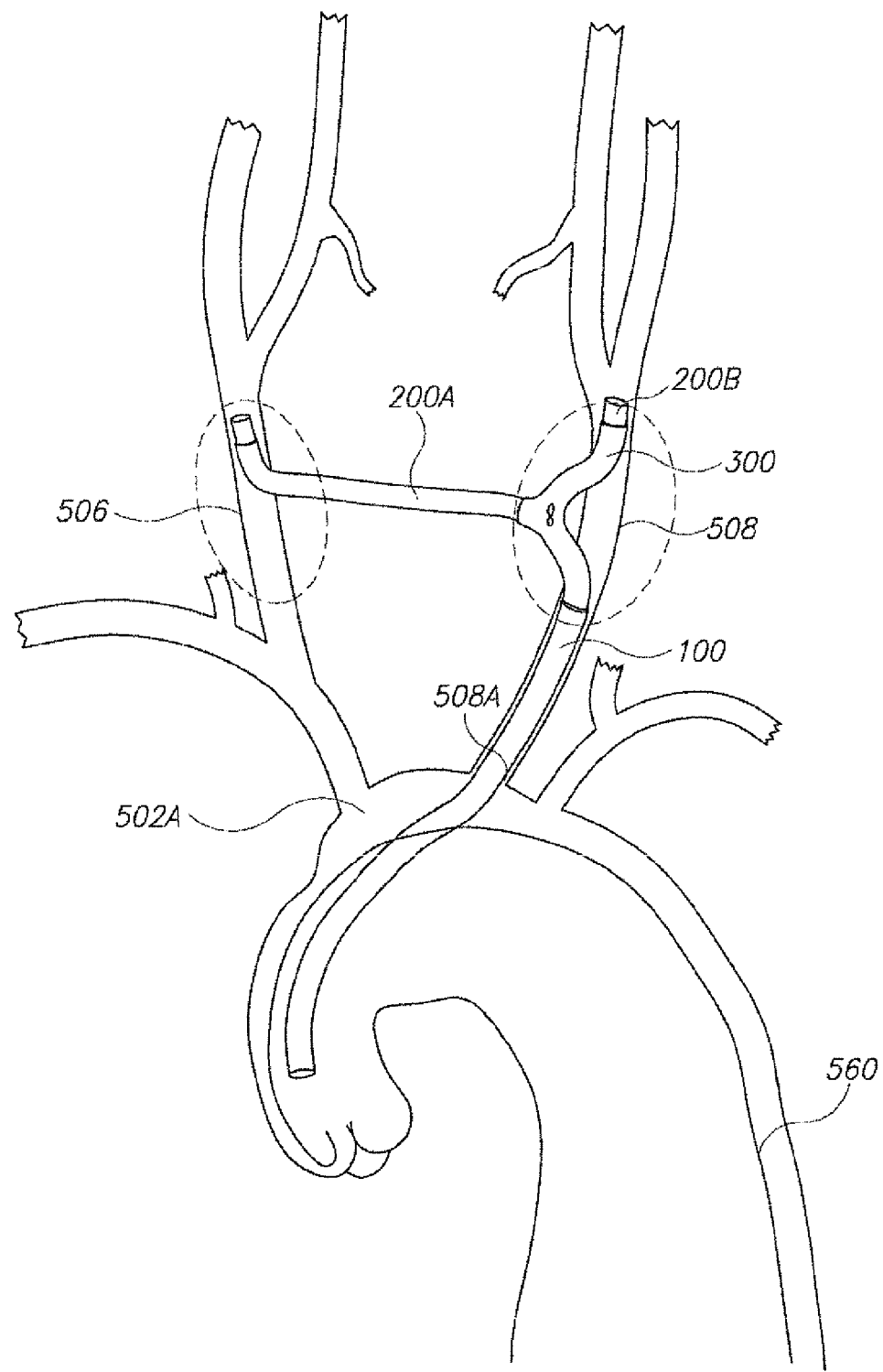
FIG. 5A is a schematic illustration of an aorta with a shunt connecting the ascending aorta to a BSA and two BSAs being interconnected according to an embodiment of the invention.

Connecting (22) the two BSAs (FIG. 5A) is to allow blood flow going from the aorta to one of the BSAs to feed both BSAs. This way, the two BSAs are supplied with blood although one of them is occluded by the stent-graft. The connection is optionally with a carotid perfusion catheter that goes from one BSA to the other, optionally connecting the two BSAs in the neck area, for example as shown in FIG. 5A. In the stage shown in FIG. 6, blood flows through the carotid perfusion catheter (200A) from the left common carotid artery (508) to the right common carotid artery (506).

In the embodiment of FIG. 2 there are two actions of deploying stent-graft side-branches: 24 and 26. These are required if having in the stent-graft an opening facing a side-branch of the aorta is not sufficient to ensure therapeutic efficacy of the stent-graft. Deploying a side-branch (24, 26) optionally includes creating an opening in the stent-graft, and attaching the side-branch to the stent-graft at the opening.

Figure 7:
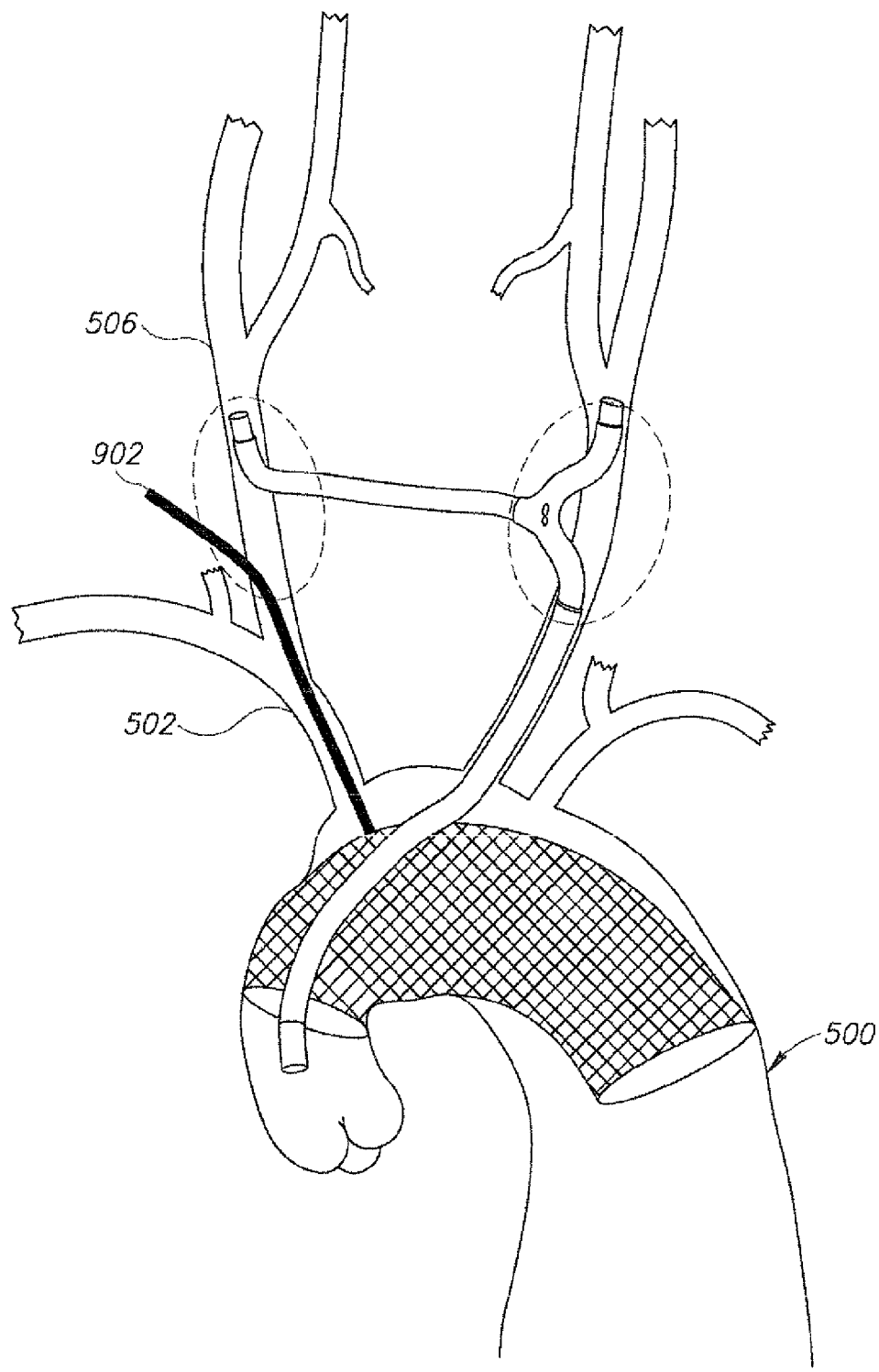
FIG. 7 is a schematic illustration showing in-situ fenestration of a stent-graft according to an embodiment of the invention.
Figure 10:
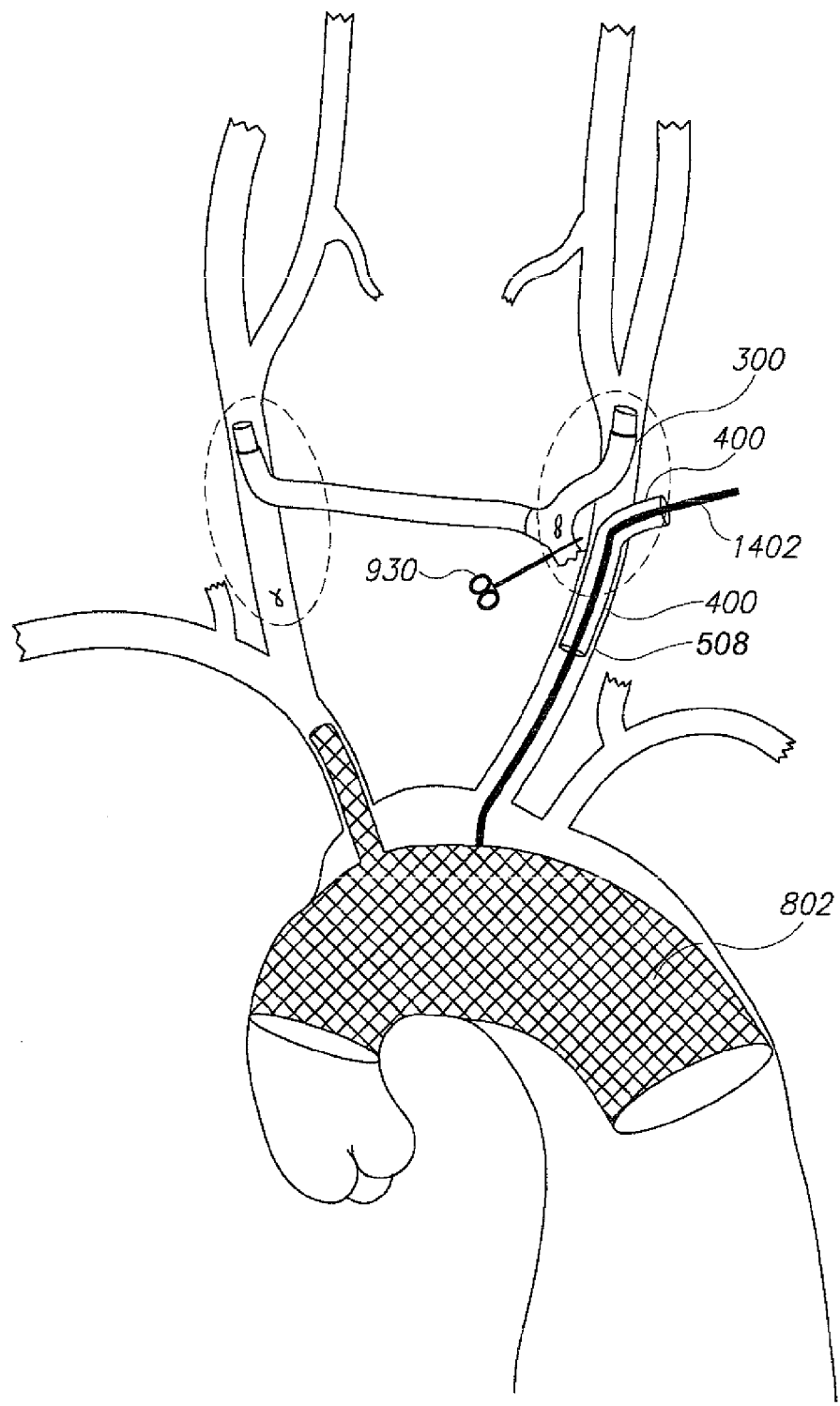
FIG. 10 is a schematic illustration of in-situ fenestration of a stent-graft aided with a valved sheath according to an embodiment of the invention.

The opening is optionally created with a fenestration instrument reaching the stent-graft through the BSA to which the side-branch should fit (FIGS. 7 and 10). Optionally, the fenestration instrument and/or the side arm are introduced through the right brachial artery or through the right subclavian artery, or from femoral arteries.

The side-branch is optionally brought to the site through the BSA via the same route and on the same guide wire that was employed during the creation of an adequately sized fenestration. Alternatively the side arm stent-graft may also be delivered from the femoral arteries or from the right brachial or subclavian artery for the innominate artery and the left brachial or subclavian artery for the origin of the left subclavian artery. Attachment of the side arm to the main stent-graft is optionally by expansion of an appropriately sized balloon-expandable stent-graft within the defect and then over dilating (trumpeting) of the portion of the side arm that protrudes into the main stent-graft lumen, so that it does not dislodge.

An Exemplary Procedure in Detail

FIGS. 3-12 schematically illustrate an aorta (500) during different stages of deploying a stent-graft in the aorta according to an embodiment of the invention.

Figure 3:
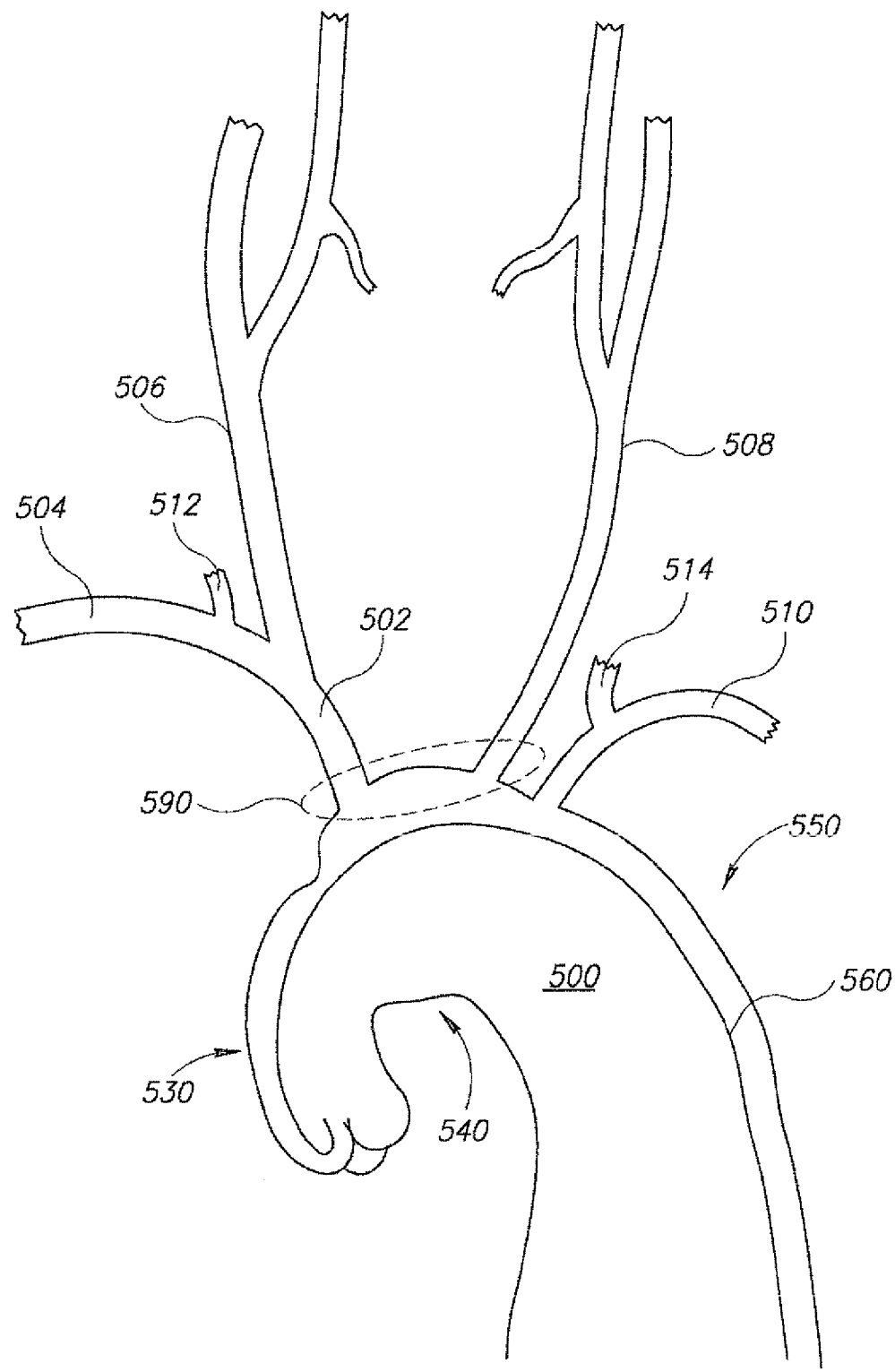
FIG. 3 is a schematic illustration of an aorta with a stiff wire inserted therein.

FIG. 3 is a schematic illustration of an aorta (500), showing different blood vessels branching from it. Blood vessels shown include the innominate artery (502), from which the right subclavian artery (504) and the right common carotid artery (506) are branching; the left common carotid artery (508); and the left subclavian artery (510). Also shown are the right (512) and the left (514) vertebral arteries. All the arteries that are numbered in FIG. 3, except for the right subclavian artery, which usually does not connect to the aorta directly, are considered in the present description and claims as brain supplying arteries. A branch stent graft is usually deployed according to embodiments of the present invention in one or more of the innominate artery (502), left common carotid artery (508), and left subclavian artery (510).

FIG. 3 also shows three main parts of the aorta (500): the ascending aorta (530), the aortic arch (540), and the descending aorta (550). The lesion to be treated is the irregularity and widening of the aorta encircled with a dashed line (590).

In a method according to an embodiment of the invention, the first action to be taken in deploying the stent-graft is puncturing a femoral artery and inserting through it a stiff wire (560) into the ascending aorta (530) so that the stent-graft can be guided on the stiff wire to the deployment location.

Figure 4:
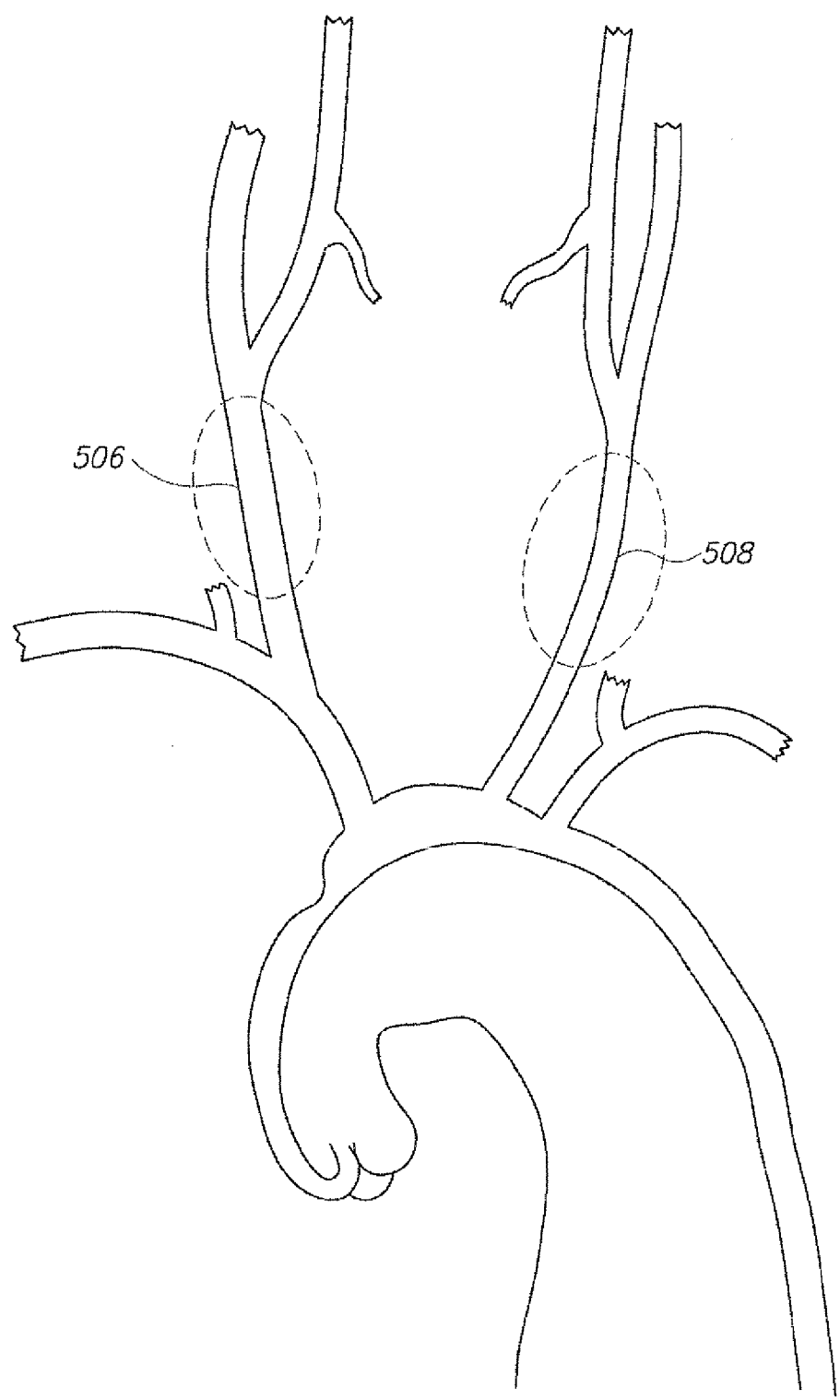
FIG. 4 is a schematic illustration of the aorta, showing possible locations for surgical exposure during a method according an embodiment of the invention.

FIG. 4 shows areas (encircled with dashed lines) in the two common carotid arteries (506 and 508) that may be surgically exposed in the neck, for inserting the removable shunt into one of them and connecting between them (22 in FIG. 2).

In FIG. 5A, the two common carotid arteries (506 and 508) are connected to each other with a carotid perfusion catheter 200A. An example to a perfusion catheter suitable for this task is provided in FIG. 13.

Figure 5B:
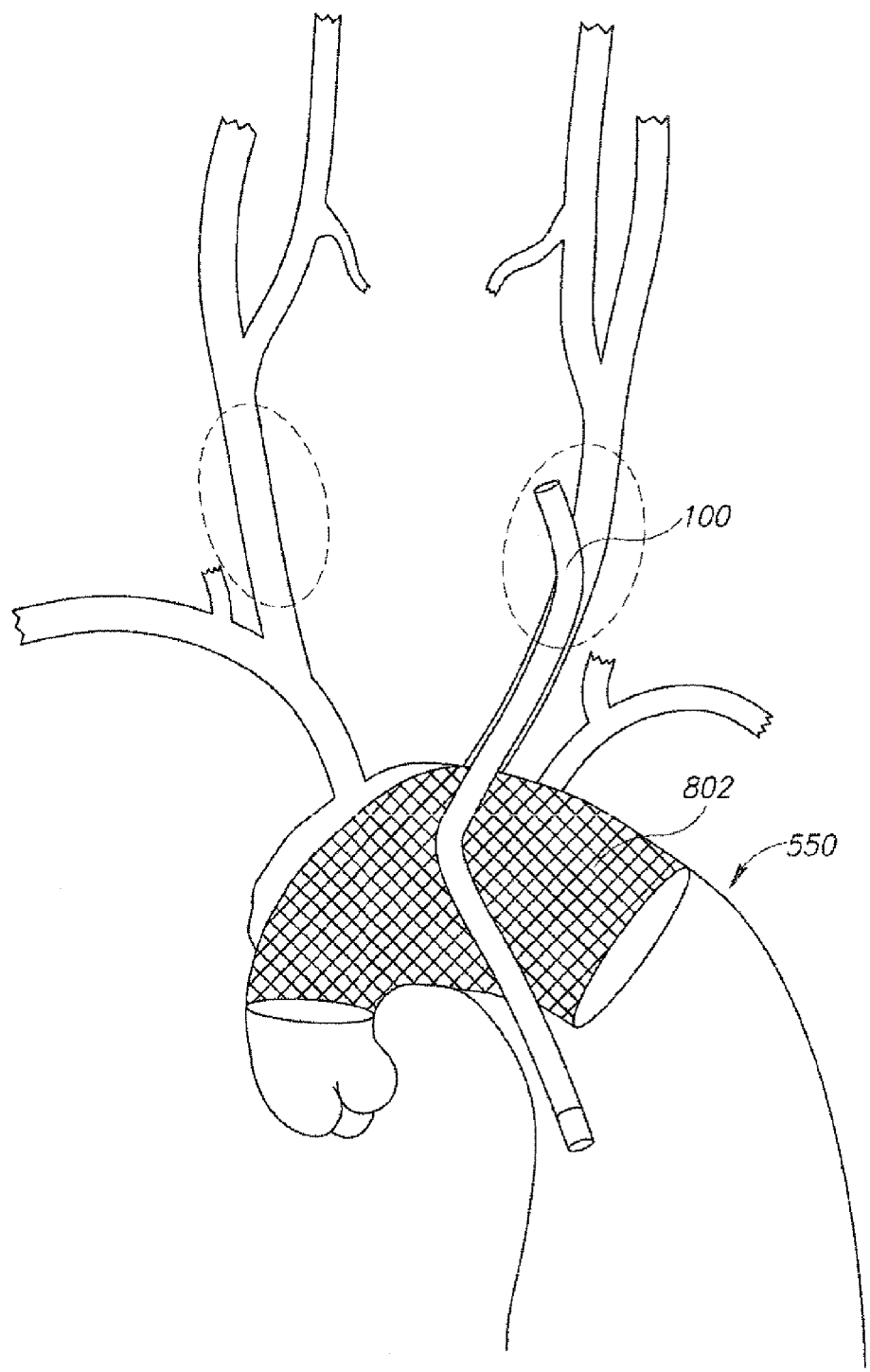
FIG. 5B is a schematic illustration of an aorta with a shunt connecting the descending aorta to a BSA and a stent-graft deployed in the aortic arch according to an embodiment of the invention.

A paraendograft shunt (100, described in detail in FIG. 16A) is inserted through the left common carotid artery into the ascending aorta (as shown in FIG. 5A) or into the descending aorta (as shown in FIG. 5B). The selection between the two possibilities is, for example, in accordance with procedure plan and anatomy. For instance, if the aneurysm extends far into the ascending aorta, the configuration of FIG. 5B may be preferred.

After the shunt (100) is inserted, heparin is administered, and the carotid perfusion catheters (200A and 200B) are inserted into the common carotid arteries (506 and 508, respectively) to interconnect the common carotid arteries, and the shunt (100) is connected (22) to the perfusion catheters with a Y-connector (300). An example of a suitable Y-connector is described in FIG. 14.

In the situation described in FIG. 5A blood goes to the two carotid arteries (506 and 508) through the shunt, and occluding the natural openings 502A and 508A by a stent-graft will not stop blood supply to the brain.

Figure 6:
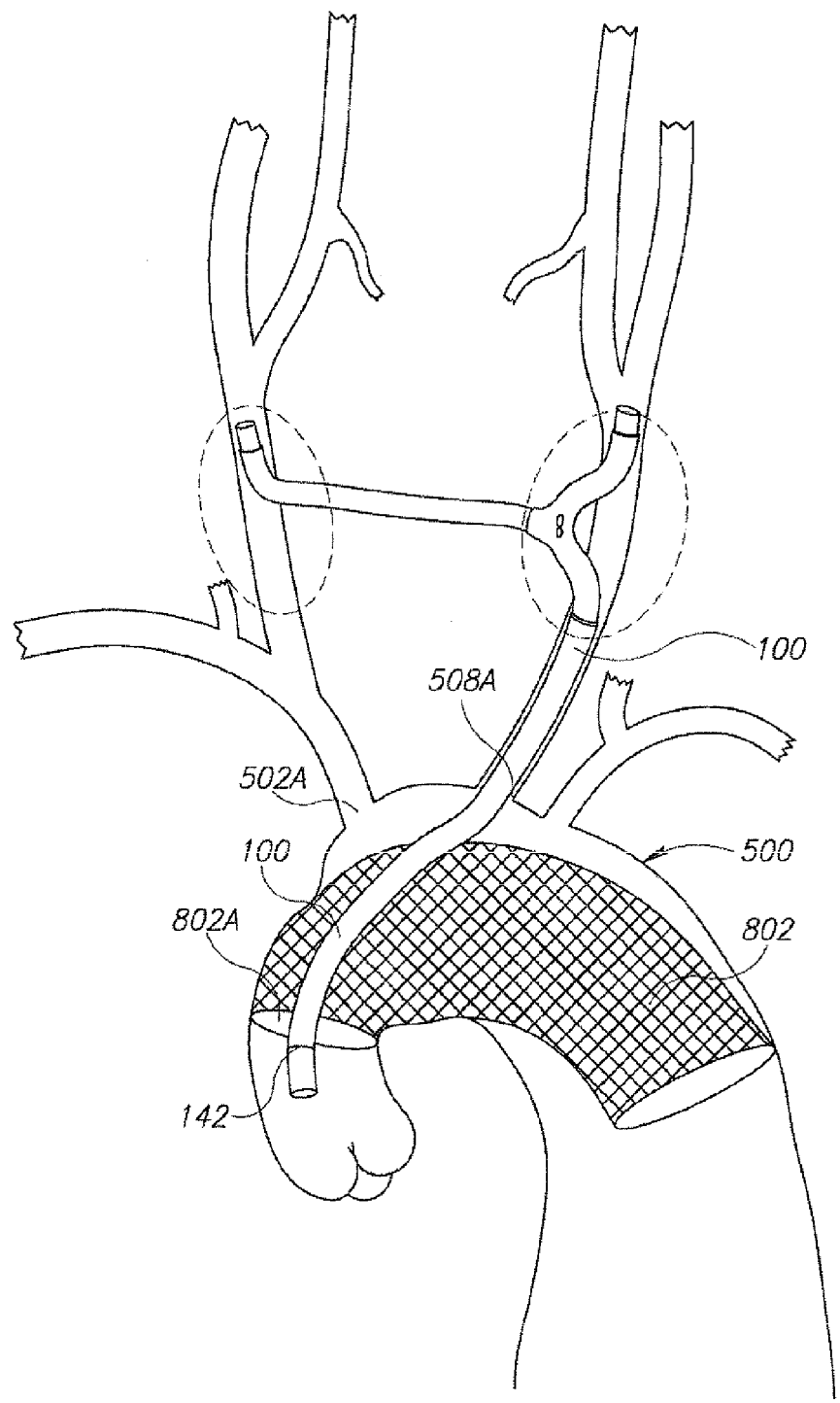
FIG. 6 is a schematic illustration of the aorta of FIG. 5A, with a stent-graft deployed according to an embodiment of the invention.

FIG. 6 shows aorta 500 with a stent-graft 802 deployed therein (14 in FIGS. 1 and 2), occluding openings 502A and 508A, while blood is supplied to the brain mainly through the shunt (100). The shunt is pressed between the stent-graft (802) along a section going from the vicinity of the opening 508A to the end (802A) of the stent-graft. The stent-graft (802) is positioned in a location determined in accordance with clinical requirements, and such that end 802A of the stent-graft, which is closest to the inflow segment (110, FIG. 16A) of shunt 100, does not extend beyond marker 142. For simplicity of presentation, stiff wire 560 is not shown in the figures following FIG. 6, but in practice it is typically removed only at the end of the procedure.

FIG. 7 relates to deploying a stent-graft side-branch in the second BSA (action 24 of FIG. 2). FIG. 7 shows aorta 500, with the right common carotid artery (506) punctured, and a fenestration instrument (902) inserted through the punctured artery to construct an opening for a stent-graft side-branch that would go into the innominate artery (502). The fenestration instrument may be, for instance, a needle from a multi-purpose drainage set (Rocket Medical, Washington UK), or a Rosch-Uchida transjugular needle (Cook, Bloomington, Ind.).

In other embodiments of the invention, openings and/or side-branches may be prepared before the stent-graft is deployed. In one embodiment, openings in the stent-graft are made before deployment, and these openings are aligned with the BSAs during deployment. In an embodiment of the invention, one opening is pre-made and is aligned during deployment, while another opening is made in situ. Similarly, one or more side-branches may be pre-made integral with the stent-graft and extended during deployment. In all these cases, using the paraendograft shunt (100) allows the surgeon longer time for aligning and/or creating openings facing the BSAs and/or extending the side-branches to fit into the BSAs.

Figure 8:
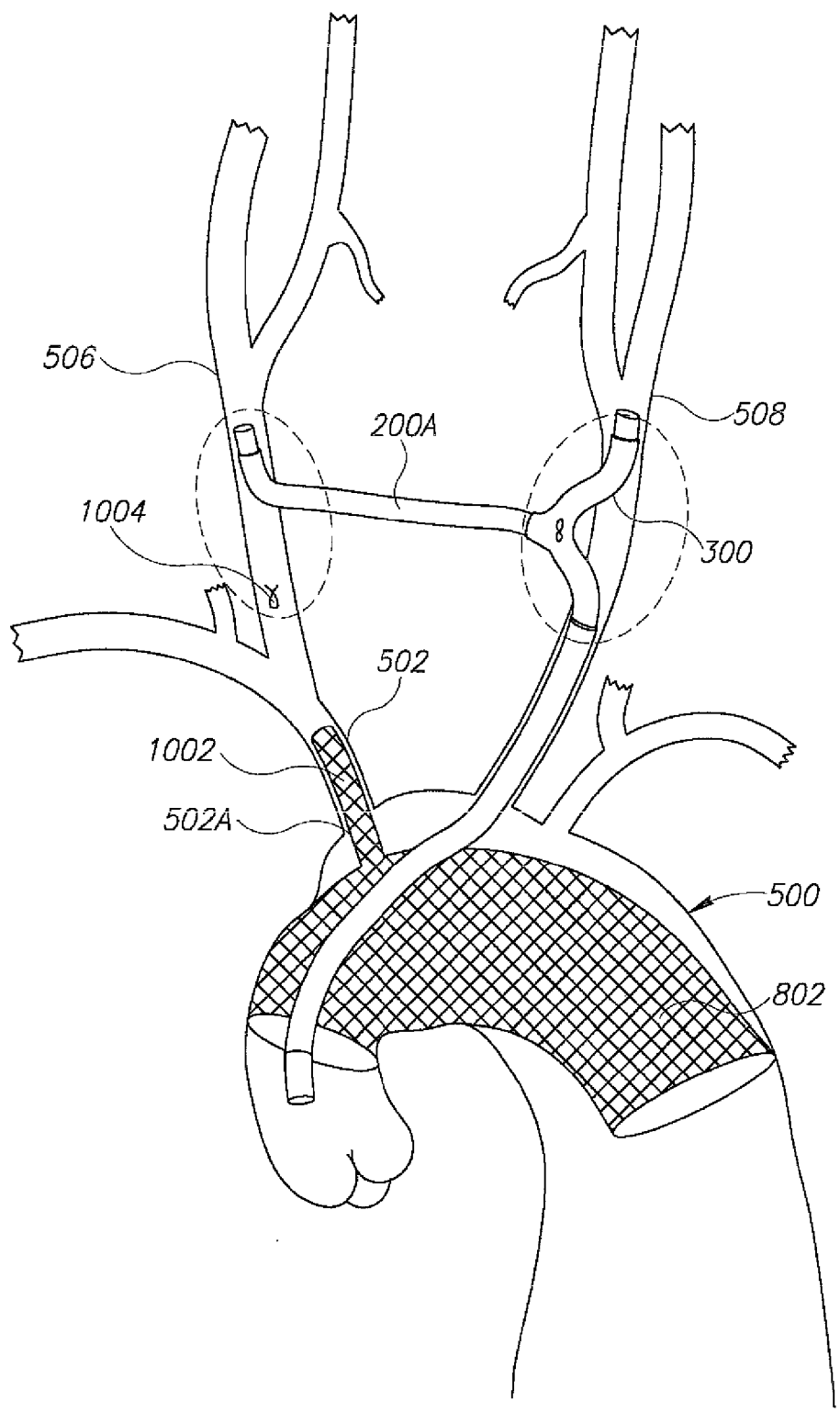
FIG. 8 is a schematic illustration of a stent-graft deployed in the aorta and having a side-branch going to a BSA according to an embodiment of the invention.

FIG. 8 shows aorta 500 with stent-graft 802, when the stent-graft has a side-branch 1002. Side-branch 1002 may be inserted with a catheter from a femoral artery through the stent-graft (802) into the innominate artery (502) or via the carotid artery by the same route as the fenestration device or from the right brachial or subclavian arteries, and connected to the stent-graft at the vicinity of opening 502A. Before insertion of side-branch 1002, and if the branch is inserted from the carotid it is optionally advanced on the wire that was before used for the fenestration instrument. When the puncture in the artery is no longer required, it is sutured with a suture 1004.

Figure 9:
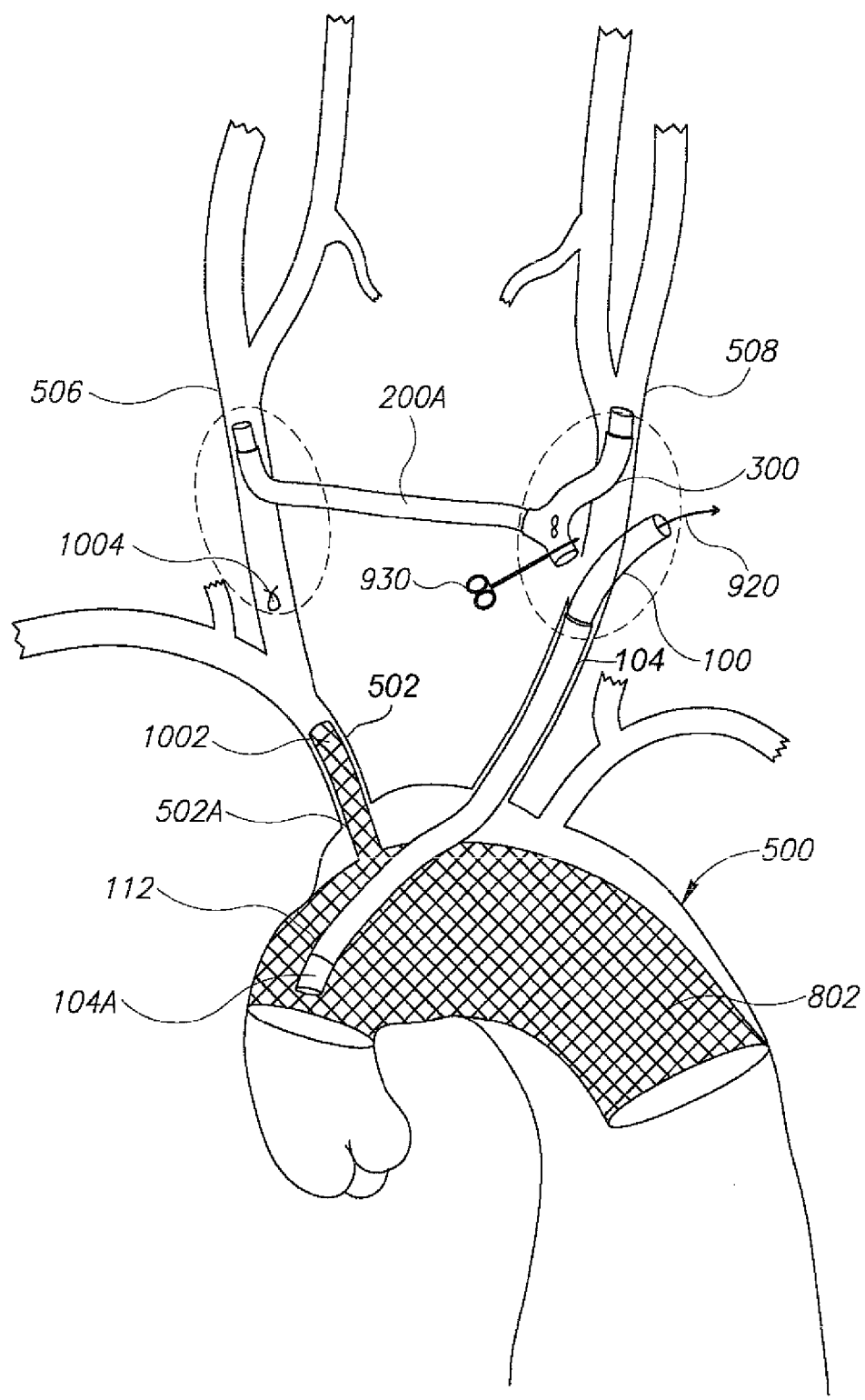
FIG. 9 is a schematic illustration of a stent-graft deployed in the aorta and having a side-branch going to a first BSA and a shunt being pulled out through another BSA, according to an embodiment of the invention.

When the side-branch is ready, the shunt may be removed (16), as both carotid arteries are supplied with blood through the innominate artery (502). FIG. 9 shows removal of the shunt, and FIG. 10 shows aorta 500 after removal of shunt 100. When the shunt is removed, part of the blood going from the innominate artery (502) to the right common carotid artery (506) flows towards the left common carotid artery (508) through carotid perfusion catheter 200A. In the embodiment shown, this requires that there be sufficient space between the front end of the right carotid perfusion catheter and the artery wall so that blood flowing into the common carotid artery from the innominate artery can enter the right carotid perfusion catheter and perfuse the left carotid.

Removing the paraendograft shunt (100) from the aorta is a delicate step, since the shunt is pressed between the aorta and the stent-graft, and must be taken out without dislodging the stent-graft.

FIG. 9 shows aorta 500 while shunt 100 is being pulled out in the direction of arrow 920. The Y-connector 300 is disconnected from the shunt and sealed with a tube clamp 930. The figure also shows the front end 112 of shunt 100 and the front end 104A of an inverted sleeve 104 during pull-out of the shunt. The inverted sleeve and various other portions of shunt 100 are shown in detail in FIGS. 16A-16C.

FIG. 10 shows aorta 500 after shunt 100 was pulled out, after being disconnected from the Y-piece (300), leaving the cross carotid catheter (200A) in place for shunting blood from right to left.

FIG. 10 also shows a fenestration instrument 1402, which is optionally inserted through artery 508, for building another side-branch (26, FIGS. 2 and 1202, FIG. 11) to stent-graft 802. It may be advisable to insert fenestration instrument 1402 through a short wide valved sheath (400, see FIG. 15), in order to occlude the opening of the aortic shunt, and enable work within the artery.

Figure 11:
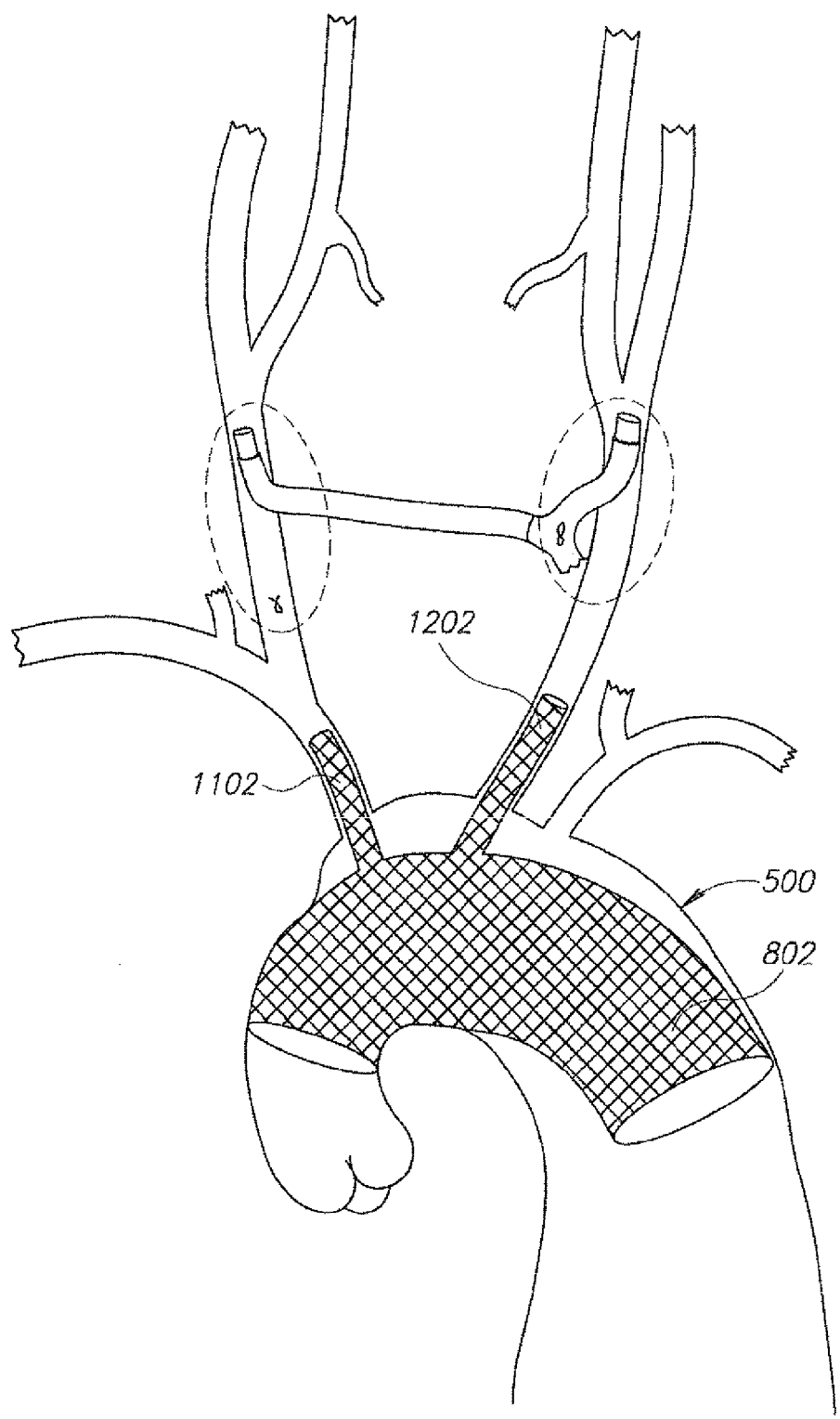
FIG. 11 is a schematic illustration of an aorta with a stent-graft having two side-branches deployed therein according to an embodiment of the invention.

FIG. 11 shows aorta 500 with a stent-graft having two side-branches (1102 and 1202).

Figure 12:
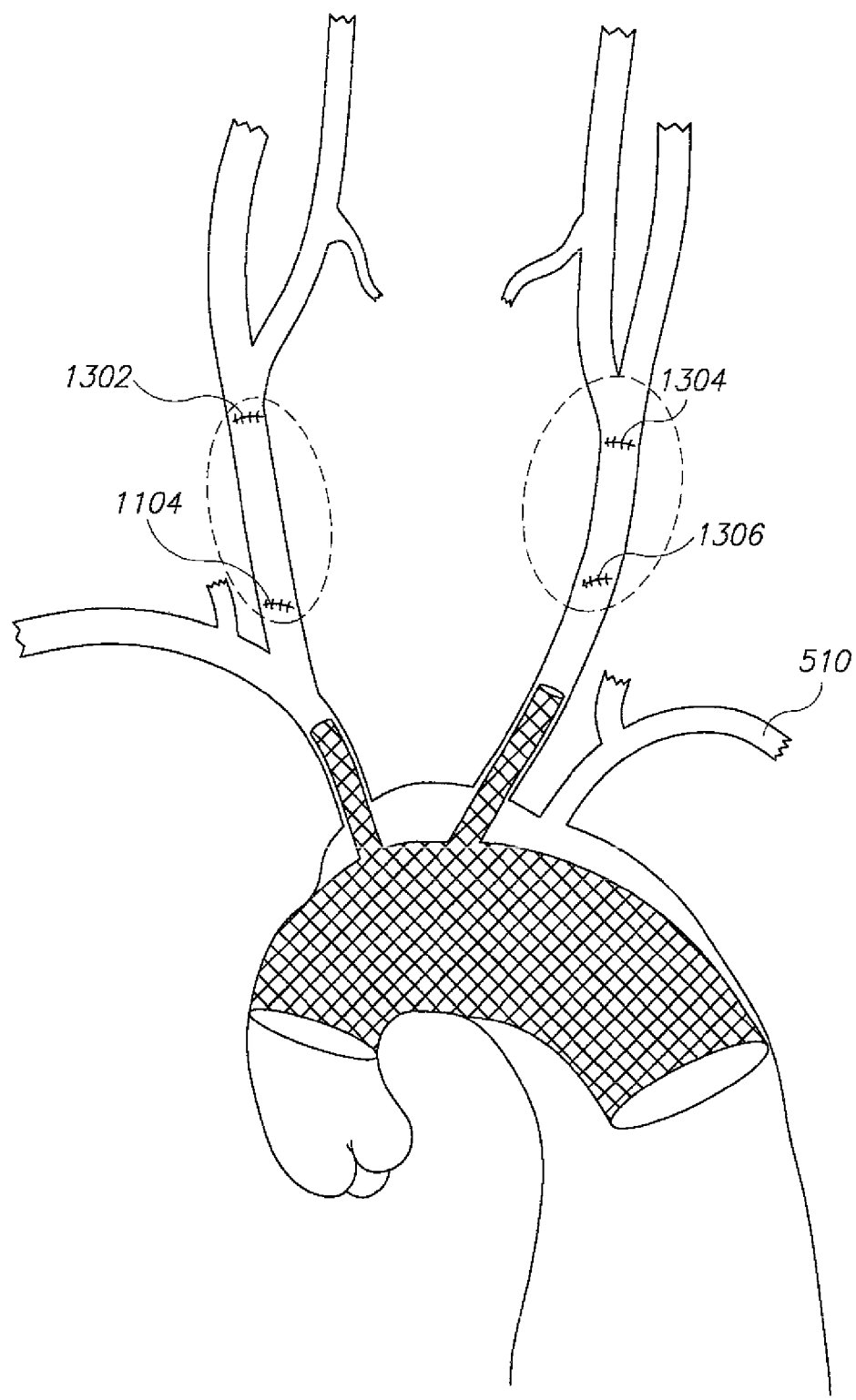
FIG. 12 is a schematic illustration of an aorta with a stent-graft deployed therein according to an embodiment of the invention.

FIG. 12 shows the same aorta, after the carotid perfusion catheters have been removed and the defects in arteries sutured (see sutures 1104, 1302, 1304, and 1306). The sutures may be all the same, as shown in FIG. 12. Optionally, some of the sutures may be smaller than others, as suture 1004 is illustrated to be in FIG. 8. The left subclavian artery is a brain-supplying artery, the origin of which may be left covered with impunity, at least with patients of normal anatomy. In some cases, however, constructing a side-branch in the left subclavian artery is also required.

At the stage illustrated in FIG. 12, the aortic defect repair may be continued with additional stent-graft pieces as required. Often, they are required in the descending aorta (550).

Useful Devices

Carotid Perfusion Catheter

Figure 13:
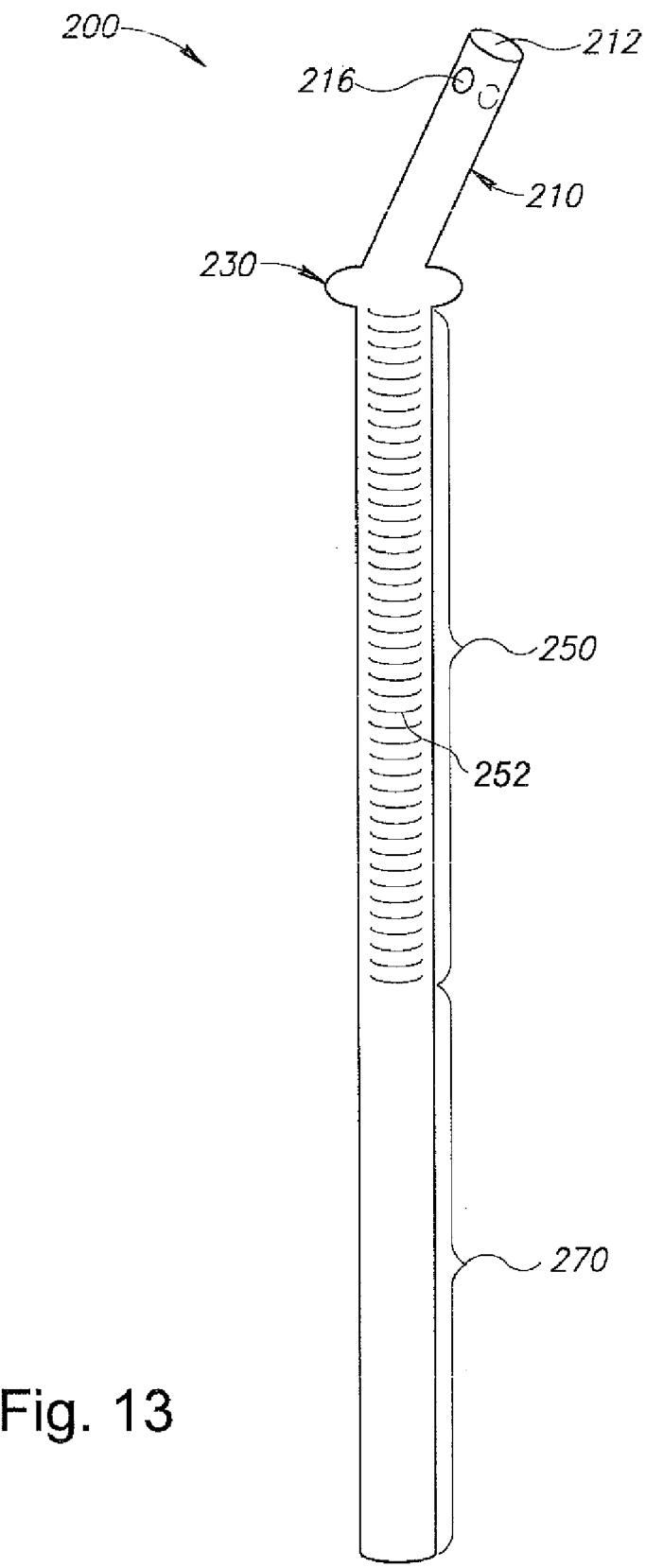
FIG. 13 is a schematic illustration of a carotid perfusion catheter according to an embodiment of the invention.
Figure 14:
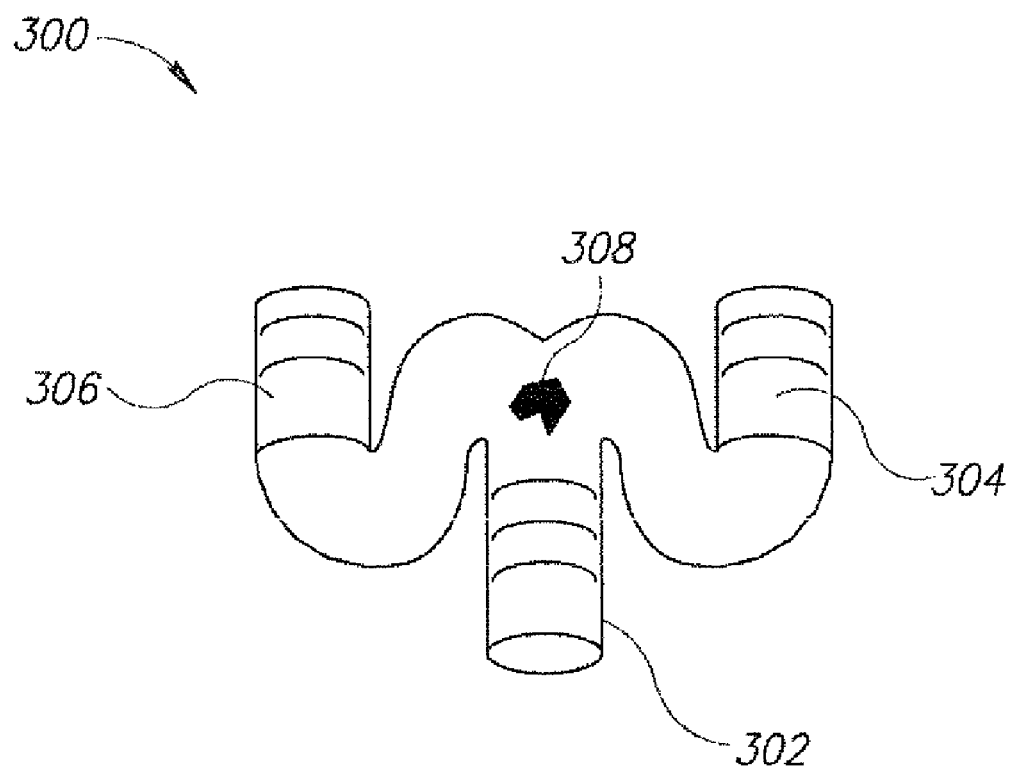
FIG. 14 is a schematic illustration of a branched connector according to an embodiment of the invention.

FIG. 13 is a schematic illustration of a carotid perfusion catheter (200) suitable for connecting the two common carotid arteries as depicted in FIG. 5A, when used together with a Y-piece as shown in FIG. 14. The two perfusion catheters 200A and 200B, shown in FIG. 5A, may be of different lengths, however, their general structure may be similar, and in an embodiment of the invention, this general structure is as illustrated in FIG. 13.

The carotid perfusion catheter (200) is shown to have 4 segments: a front segment 210, an intermediate segment 230, a reinforced segment 250, and a back segment 270.

The front segment (210) has a distal open tip (212) and tapered edges. Along about 0.5-2 cm from the tip, the front segment is perforated, for instance by 2-4 side-holes (216) in a staggered configuration. The edges (not shown) of the side holes (216), are also tapered. This segment is moderately soft and deformable but not floppy, so that it does not injure the inside of the artery but maintains its tubular form within the artery. Front segment 210 optionally has an outer diameter of 4, 5 or 6 mm with wide end-hole 212 and tapered edges.

The front segment may be angled relative to the rest of the catheter, but is not necessarily so.

The intermediate section (230) is a short (about 1 cm) stop, designed for preventing deep insertion of the catheter into the blood vessel and aiding in fixation of the catheter in relation to the blood vessel into which it is inserted.

The reinforced segment (250) is a flexible segment reinforced with a spiral metal support (252). The reinforcement is for allowing segment 250 to be bent or looped to accommodate the position of the carotid insertion relative to the Y-connector (300, FIG. 14) without kinking and obstructing blood flow inside it. The reinforced segment has an outer diameter at least as large as the front segment, and the same as the back segment to fit the Y-connector. Typically, this is about 7 or 8 mm.

The back segment (270) optionally has a diameter identical to that of the reinforced segment (250). The back segment is devoid of spiral support, cuttable, and flexible enough to be connected to a suitably sized rigid plastic connector.

The carotid perfusion catheter is mountable on a flexible introducer with a short sharp tip and a 0.038" center cannel.

Y-Connector

FIG. 14 is a schematic illustration of Y-shape connector (300), suitable for use in connecting between two carotid perfusion catheters in a procedure according to some embodiments of the invention.

The Y-shaped tube connector (300) is wide-angled, with a short arm (302) made to fit to shunts of several sizes. In an exemplary embodiment of the invention, the short arm (302) has a length of about 8 mm. The connector (300) also has two arms (304, 306) shaped as an S or as a loop, for pointing catheters in desired directions while keeping the connector small. The arms 304 and 306 are preferably sized to fit to carotid perfusion catheters, of the kind described in FIG. 13, which requires they have a diameter of about 7 mm. In the middle of the Y, shown is a vent (308) with a cap or occluder (not shown). The vent is for removal of air and debris from the connector.

Valved Sheath

Figure 15:
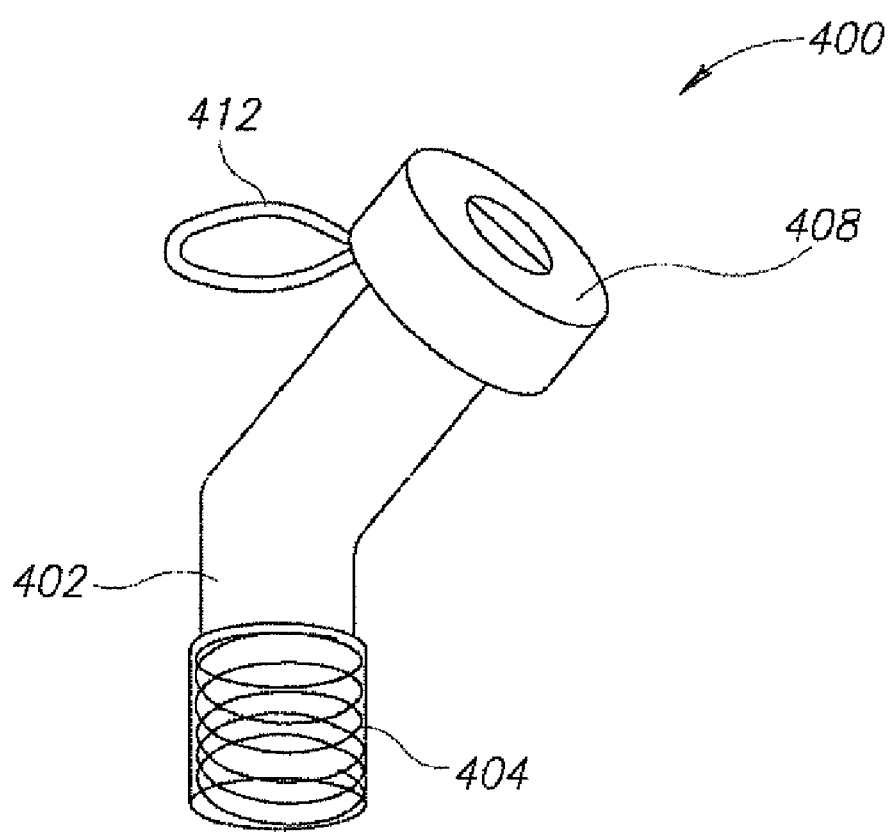
FIG. 15 is a schematic illustration of valved sheath according to an embodiment of the invention.

FIG. 15 is a schematic illustration of a valved sheath (400), suitable for use in inserting a fenestration instrument through a brain supplying artery in a procedure according to some embodiments of the invention.

The valved sheath (400) comprises a catheter (402), which may be supported by a spiral metal (404), but is not necessarily so. The sheath (400) is a catheter, having dimension of about 5-8 mm wide, for instance, 6 mm wide (outer diameter) and 2-5 cm long, for instance, 3 cm. The width is designed to fit to the inner diameter of the artery to which the sheath penetrates, and the length is designed to be shorter than the distance between the proximal end of the branch graft (for instance, 1202 of FIG. 11 or 1002 of FIG. 9) and the distal end of valved sheath 400. On the back end of the catheter (400) there is a large valve (408) for insertion of endovascular instruments, such as a fenestration instrument (1102 in FIG. 10) or a stent-graft (1202 in FIG. 11). At the base of the sheath (400) there is a noose (412) for fixation of the sheath to the carotid artery against dislodgement or accidental removal.

Paraendograft Shunt

Figure 16A:
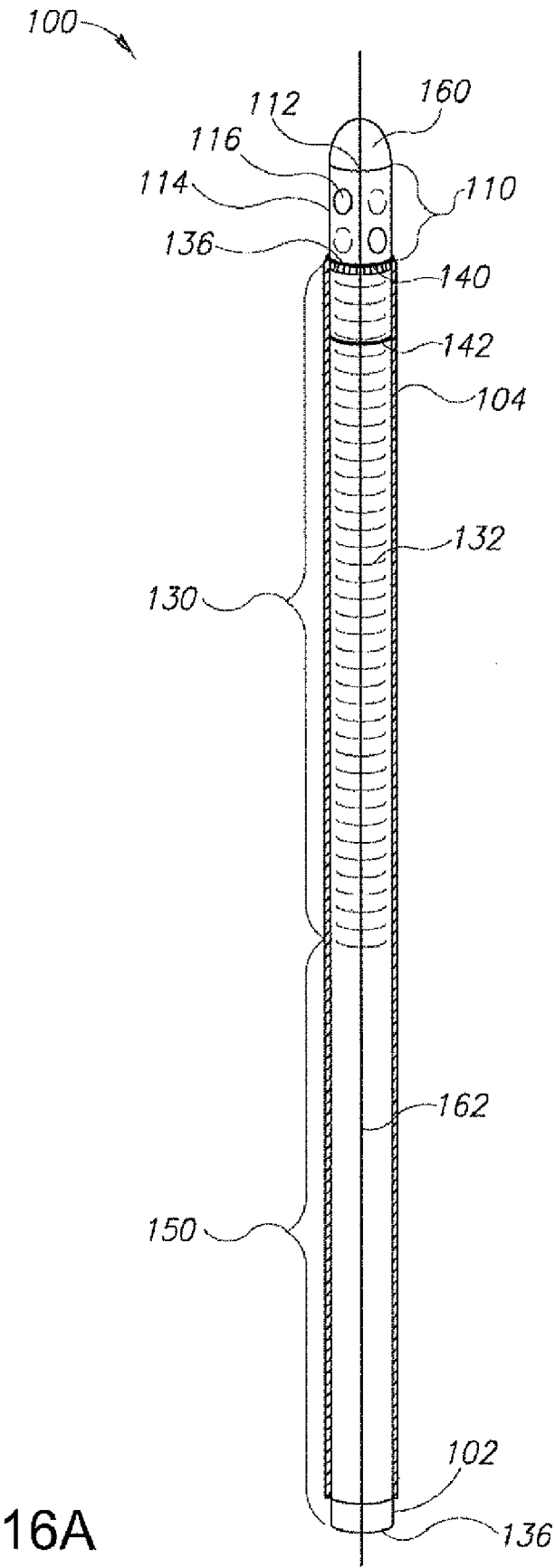
FIG. 16A is a schematic illustration of a paraendograft shunt according to an embodiment of the invention.

FIG. 16A schematically shows a removable shunt (100) with safe removal facilitating mechanism (sleeve 104) according to an embodiment of the invention.

To facilitate safe removal of shunt 100 from between the aorta wall and the stent-graft, an outer, soft, thin sleeve (104) is attached circumferentially to the catheter wall (102), such that upon pulling the shunt out of the space between the aorta and the stent-graft the shunt causes sleeve 104 to invert (see FIG. 16B) to leave an empty inverted sleeve (104A) as sleeve 104 follows the shunt out. When removal begins, the inner surface of the sleeve will slide against the outer surface of the shunt; later in the removal, more and more of the sleeve slides against itself. It is therefore optionally preferred that both surfaces of the shunt and the sleeve and the sleeve with itself form low-friction interfaces. Furthermore, the sleeve has to be made of a strong enough material not to tear apart when the shunt is pulled out, for instance, polyethylene terephthalate (PET).

In the embodiment of FIG. 16A, shunt 100 has 3 segments along its length: a front, perforated, segment (110), a middle, stiff, segment (130) and a back segment (150), that are described in further detail below. The sleeve (104) is attached to the catheter at the border between the perforated segment (110) and the spiral supported segment (130).

In an exemplary embodiment, the attachment site (136), at which the sleeve (104) is attached to the catheter (100) is indented, so that the folded portion of the sleeve does not protrude out of the profile of the catheter. And the front end of the sleeve is already folded so that the fold need not be created at the initiation of removal.

In an exemplary embodiment, the above-described circular attachment between the sleeve and the catheter is the only attachment between them.

Optionally, within the wall of the sleeve, longitudinal reinforcement wires (not shown) run along the catheter axis, to prevent disruption to the removal of the shunt. Such reinforcement wires are preferably very flexible but resistant to tearing, and may be made, for instance, of Kevlar™.

The length of the shunt (100) should be sufficient to go from within the aorta, where the distal tip (110) has to be deployed, to the neck of the patient, from which the shunt is inserted, leaving extra length from manipulating of the shunt from outside the body. Accordingly, the shunt is between about 20 cm long and 50 cm long, for instance, 20, 25, 30, 40, 45, 50 cm long, or any intermediate length. Longer shunts may also be useful, especially if the back segment of the shunt is cuttable.

The outer diameter of shunt 100 is optionally designed to be as wide as possible while still fitting into the brain-supplying artery portion along which the shunt should run during the stent-graft deployment. Alternatively, the shunt has the narrowest diameter that still allows supplying sufficient blood flow to the brain during stent-graft deployment. Depending on the dimensions of the patient, the outer diameter of the shunt (100) is optionally between about 5 mm and about 8 mm, for instance 5, 6, 7, or 8 mm. The wall (102) of the catheter (100) is preferably thin to maintain a maximal inner lumen. The outer surface of the wall (102) is optionally smooth and hydrophilic to assist in insertion and/or removal of the shunt.

Figure 16B:
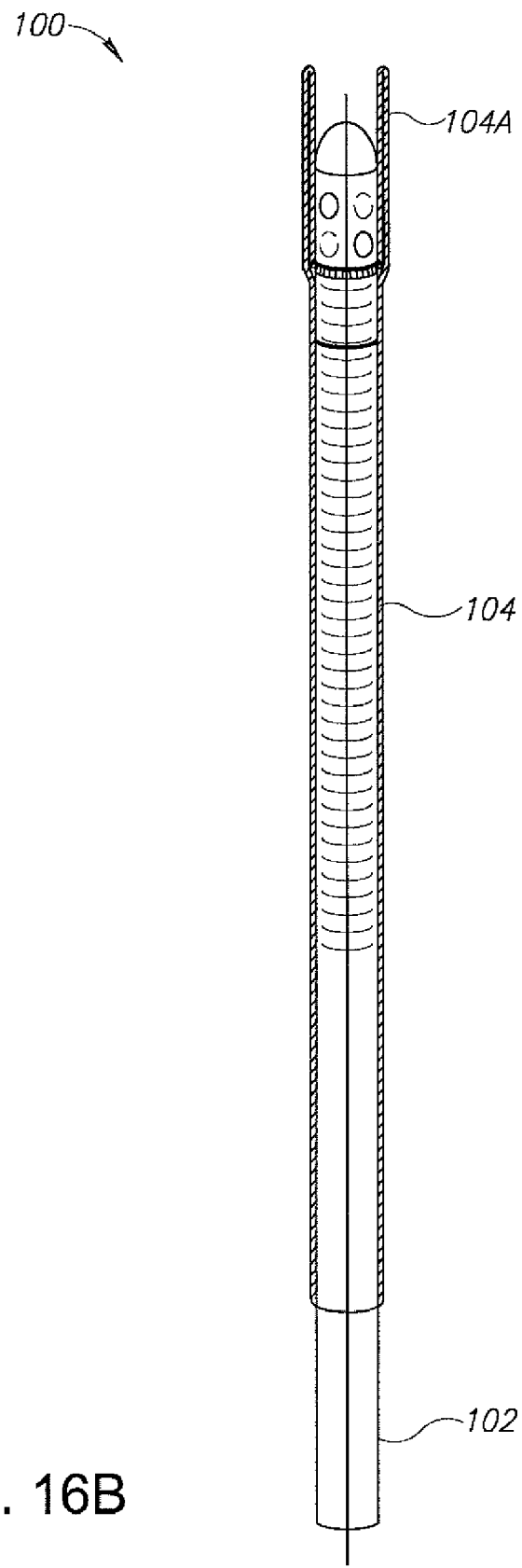
FIG. 16B is a schematic illustration of the paraendograft shunt of FIG. 16A, with partially inverted sleeve.
Figure 16C:
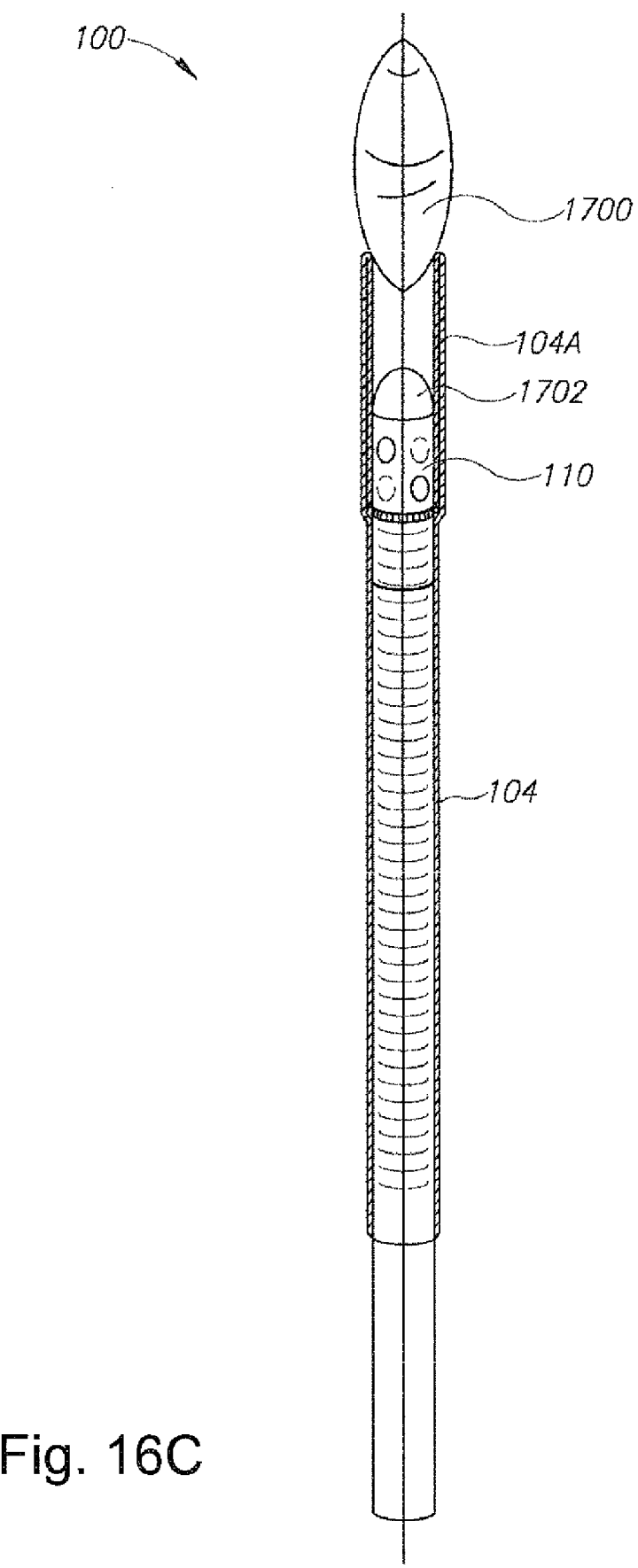
FIG. 16C is a schematic illustration of paraendograft shunt of FIGS. 16A and 16B, with a balloon protruding in front of it.

The front segment (110) has a distal open tip (112) that allows delivering a balloon (1700 in FIGS. 16C and 17) through the shunt, when the shunt is equipped with a suitable introducer (1702 in FIG. 16C). The front segment has tapered edges (114) to prevent tissue injury during insertion of the shunt. The front segment is optionally about 1-2 cm long, and is perforated by sideholes (116) in a staggered configuration, for allowing blood flow into the shunt if the tip is occluded. The edges of the side holes are optionally tapered, so as not to scrape the inner surface of a diseased aorta.

The front segment (110) of the shunt (100) is moderately soft and deformable so that it does not injure the inside of the aorta; yet, the front segment is not floppy, so that it does not fold or bend with the blood flow. Examples to commercially available catheters having the required deformability and floppiness are aortic cannulas used in open surgical cardiopulmonary bypass.

Also shown in the figure are markers (140, 142), which allow a surgeon to locate the tip of the shunt during operation, and particularly during insertion and removal of the shunt. Marker 142 is located on the middle segment, to help in positioning the shunt and the stent-graft in respect to each other. Marker 140 is positioned to be at the most distal point to which the stent-graft can get along the shunt (100) without occluding. Marker 142 may also be useful in positioning the shunt and the stent-graft so there will be no direct contact between the stent-graft and the non-sleeved front-end (110) of the shunt. This way, removal of the shunt does not initiate friction between the shunt front-end and the stent-graft. In the embodiment shown, the distance between marker 140 and the tip of the shunt is about double the length of the front segment (110). Markers 140 and 142 are preferably of a kind that is readable from outside the body, for instance, a radio-opaque marker.

The middle, stiff, segment (130) is the segment to be pressed between the stent-graft and the aorta. Accordingly, depending of the physical dimension of the patient, it is optionally between about 15 and about 30 cm long, for instance: 15, 20, 25, 30 cm, or any intermediate length.

The middle segment is designed to withstand the compressive force that would be exerted on it during the stent-graft deployment while retaining large enough a volume to allow sufficient blood flow through it to the brain. Typically, this requires that the middle segment withstands compressive force of 1 kg per cm length of compressed catheter segment with a deformation of at most 10%. In the embodiment shown, this is achieved by supporting the middle segment (130) with a metal spiral (132) running within the wall (102) of the shunt (100).

The back segment (150) is optionally devoid of spiral metal support. It is preferably moderately soft and clampable, cuttable with heavy scissors and flexible enough to be attachable to an appropriately-sized plastic connector, so it can be cut to size, connected to the Y-piece, and—after its removal—cut short and clamped adjacent to the Y-piece so that the blood can flow from right to left (see FIG. 9).

The shunt (100) is mountable on each one of two flexible introducers, each having a short blunt tip.

One of the introducers (160 in FIG. 16A), which is for regular use, optionally has a 0.038" central channel for a guidewire (162). The other introducer has a 6F central channel and a valve at the back end, such that it is suitable for insertion of a balloon catheter.

Figure 17:
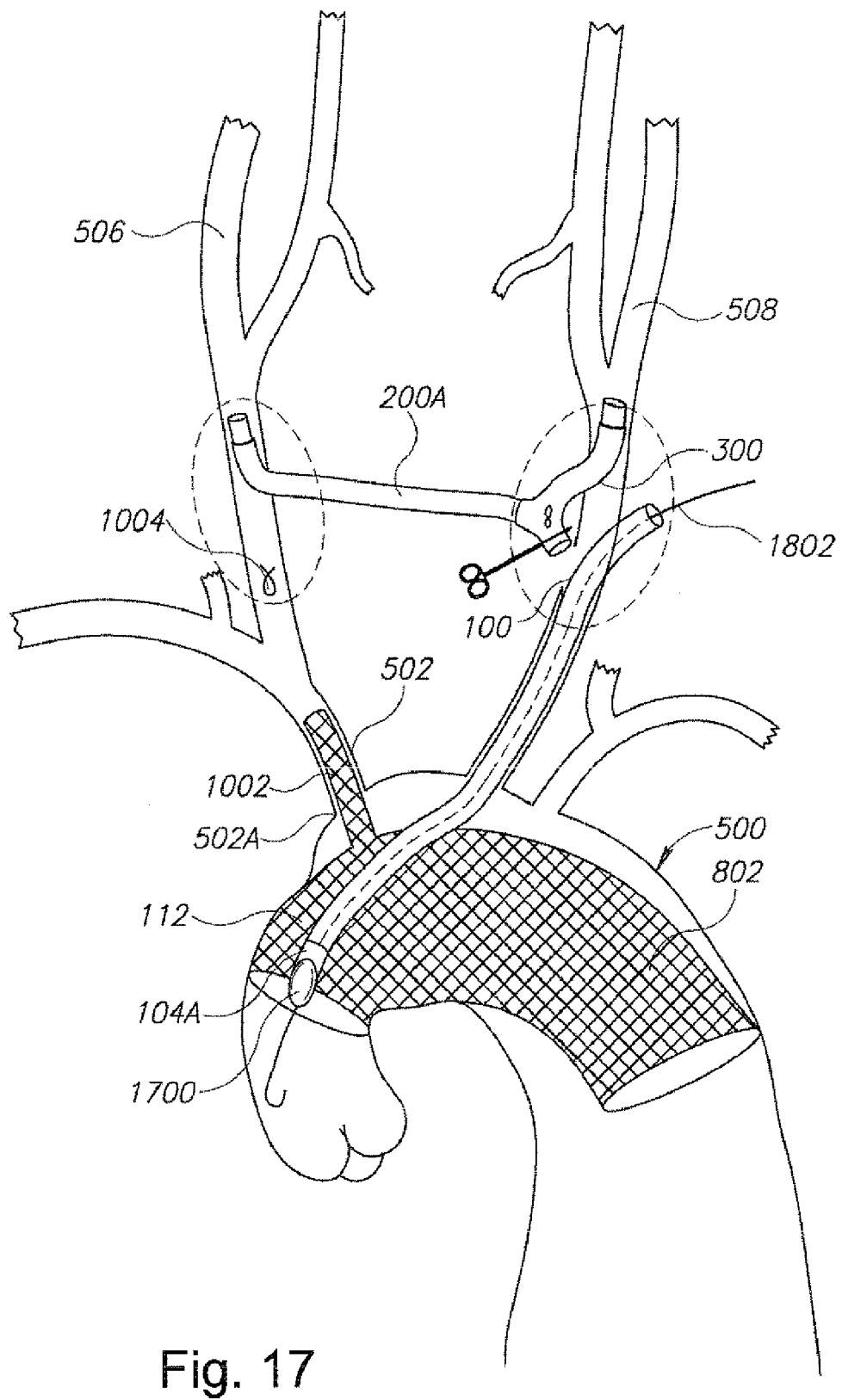
FIG. 17 is a schematic illustration of a stent-graft deployed in the aorta and having a side-branch going to a first BSA and a shunt being pulled out from a second BSA with the aid of a balloon, in accordance with an embodiment of the invention.

FIG. 16C shows a paraendograft shunt having a removal-facilitating mechanism, additional to the inverted sleeve. Its use according to an embodiment of the invention is illustrated in FIG. 17. According to this embodiment, if for any reason, the shunt (100) is stuck on its way out, a balloon 1700 (which rides on guidewire 1802) may be inserted between the aorta (500) and the stent-graft (802) to reduce pressure that the stent-graft and the aorta exert on the shunt, thereby facilitating safe removal of the shunt. Optionally, the balloon is a standard angioplasty balloon.

When a shunt of the kind illustrated in FIG. 16A is used, its removal happens in two stages: first, as shown in FIG. 16B, the body of the shunt (102) is pulled from the sleeve (104), which is inverted to leave an empty inverted sleeve (104A) pressed between the aorta and the stent-graft, and then the sleeve is pulled. Optionally, a balloon 1700, is introduced through the shunt (100) to help releasing the shunt. This is shown in FIG. 17.

Improved Seal Stent-Graft

According to some exemplary embodiments of the invention, a stent graft is designed as a branch for a fenestrated aortic stent graft. The fenestration may be a simple, unsupported and possibly irregular defect in the fabric of an aortic stent graft. Optionally, the aortic stent graft is free of any leak preventing means, such as a sleeve made for receiving the branch. The branch stent graft is designed to achieve a seal with the ASG under these circumstances.

In the following, embodiments of branch stent grafts with improved seal are described, and then delivery systems for delivering them and methods for deploying them are discussed.

A Branch Stent Graft with a Flaring Stent

Figure 18A:
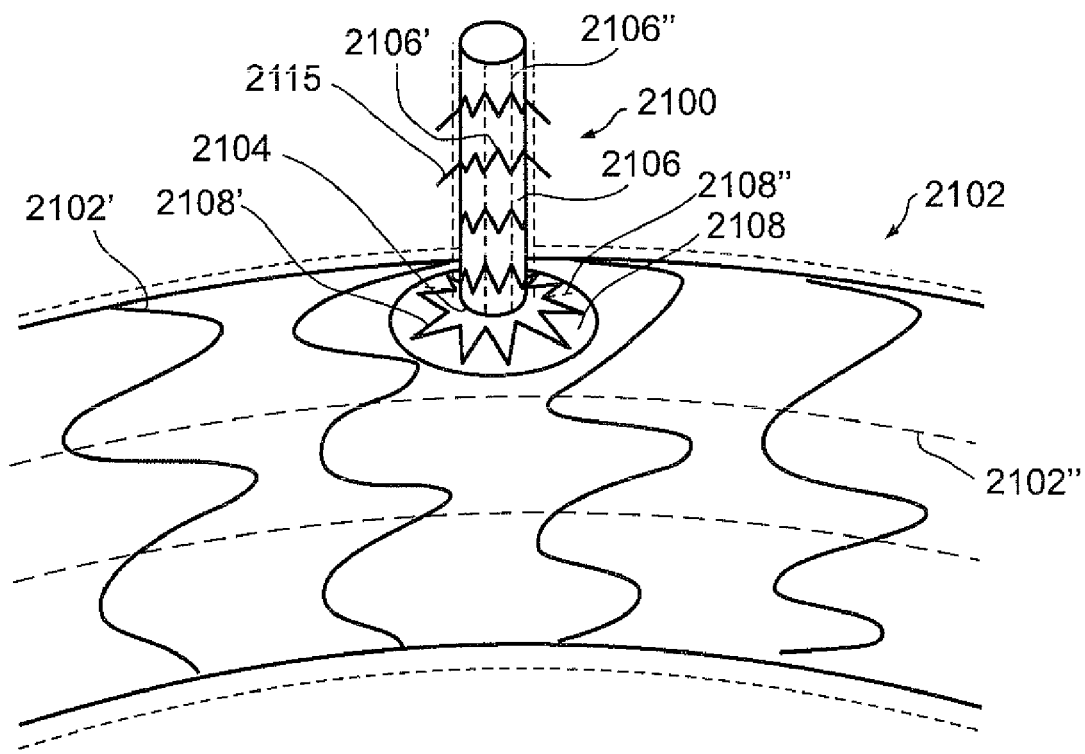
FIG. 18A is a schematic illustration of a branch stent graft according to an embodiment of the invention.

FIG. 18A is a schematic illustration of a branch stent graft (2100) sealed to an aortic stent graft (2102).

Aortic stent graft 2102 is made of a stent 2102' and a graft 2102". Graft 2102" is illustrated with dashed lines going along the outer surrounding of the aortic stent graft 2102. Optionally, the graft includes one or more reinforcement sutures (not shown) made to control propagation of a fenestration. In an exemplary embodiment of the invention, the reinforcement sutures have polygonal pattern, configured to limit and strengthen the boundary of a fenestration. Non-limiting examples of polygonal suture reinforcement patterns include hexagonal patterns and octagonal patterns.

In an exemplary embodiment of the invention, the aortic stent graft (2102) is provided with a luminal surface configured to enhance sealing of the aortic and the branch stent grafts. Optionally, the entire luminal surface of the aortic stent graft is configured for enhanced sealing. Alternatively, only portions that are expected to be in the vicinity of the fenestration are configured for enhanced sealing.

Optionally, being configured to enhance sealing includes making the luminal surface of the aortic stent graft of materials conducive to adhere to the apposing surface of the flared portion of the branch stent graft.

Alternatively or additionally, magnetic forces are used to attach the aortic stent graft and the flared portion. For this, one or both of the flared portion of the branch stent graft and the luminal surface of the aortic stent graft comprises magnetic elements attracted to metallic substances comprised in the other.

When branch stent graft 2100 is deployed together with aortic stent graft 2102 via a fenestration 2104 in aortic stent graft 2102, blood does not leak between the aortic and the branch stent grafts, or if it leaks, this leak is minute enough to be closed by clotting of the leaking blood.

Branch stent graft 2100 is designed to achieve a reliable seal with aortic stent graft 2102. Branch stent graft 2100 is made with a tubular portion 2106 and a flaring portion 2108, flaring at the proximal end of the tubular portion.

The graft portions of the tubular portion 2106 and of the flaring portion 2108 are illustrated with dashed lines going along the outer surroundings of the branch stent graft 2100.

Tubular portion 2106 of stent graft 2100 is made of a stent 2106' and a graft 2106". The graft is illustrated by dashed lines going along the outer surrounding the tubular portion 2106, to show that in the embodiment of FIG. 18A stent 2106' is inner to graft 2106". Tubular portion 2106 of stent graft 2100 is optionally short, for instance, has length ranging from 3 to 10 cm.

Flaring portion 2108 of branch graft 2100 is shown to include a stent and a graft 2108". Graft 2108" is illustrated with dashed lines that continue the dashed lines illustrating tubular graft portion 2106", to show that in this embodiment the grafts of the two graft portions are at the same side (that is, outer side) of the stent portions.

Alternatively, the stent of the tubular portion and/or of the flared portion is at the outer side of the graft. Optionally, the stent is outside the graft in one portion and inside it in another. For example, the stent may be internal to the graft in the portions further away from the flared portion (for instance, where the stent has hooks 2115), and be external to the graft nearer the flared portion. In an exemplary embodiment of the invention, tubular portion 2106 is in the form of nitinol stents made in a Z-like shape, sutured to the graft, which may be made of, for instance, polyester. Hooks (2115) pointing outward and downward are connected to the stents. Hooks 2115 may be at different levels and connected to different stents. Optionally, hooks 2115 are straight. Optionally, hooks 2115 are v-shaped.

Figure 18B:
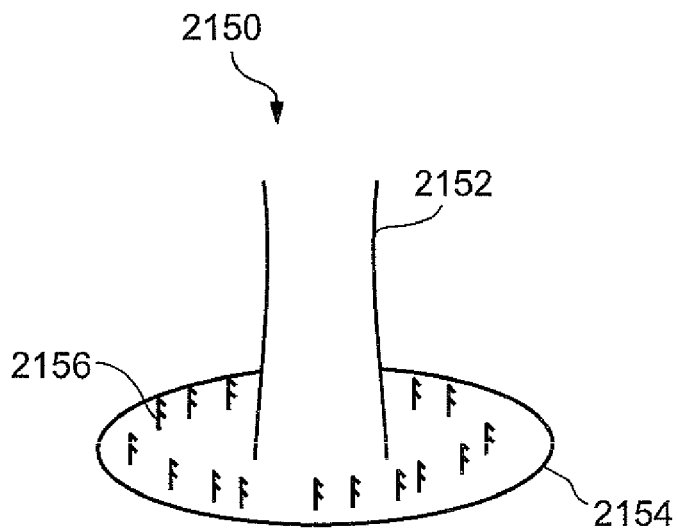
FIG. 18B is a schematic illustration of a branch stent graft having barbed flaring portion according to an embodiment of the invention.

FIG. 18B schematically illustrates a branch stent graft 2150 having a tubular portion 2152, and a flaring portion 2154 with barb-shaped hooks 2156.

Back to FIG. 18A, at fully expanded state, flaring end 2108 is substantially perpendicular to tubular portion 2106, such that it closely follows the luminal face of aortic stent graft 2102. Optionally, flaring portion 2108 is flat; alternatively, it is configured to physically closely fit the surface defining the luminal space of the aortic stent graft at the peri-fenestration area. For instance, it is optionally shaped to conform to the inside of the aortic stent graft, in which case it is flat in a first direction, intended to be deployed in the direction of the aortic stent graft, and convex (relative to the tubular part) in a second direction, perpendicular to the first.

Optionally, the ab-luminal surface of flared portion 2108 (the surface facing the aortic stent graft and not the blood) is covered with a filler, made of a biocompatible spongy matrix, for instance of polyurethane, to promote adhesion of flared portion 2108 to aortic stent graft 2102 and to induce thrombosis in the crevices between them.

Seal of flaring end 2108 to aortic stent graft 2102 is achieved with a stent-portion 2108', expanding flaring end 2108 of the branch graft, to expand it. In the embodiment shown, stent-portion 2108' is separate from tubular portion 2106.

Figure 19:
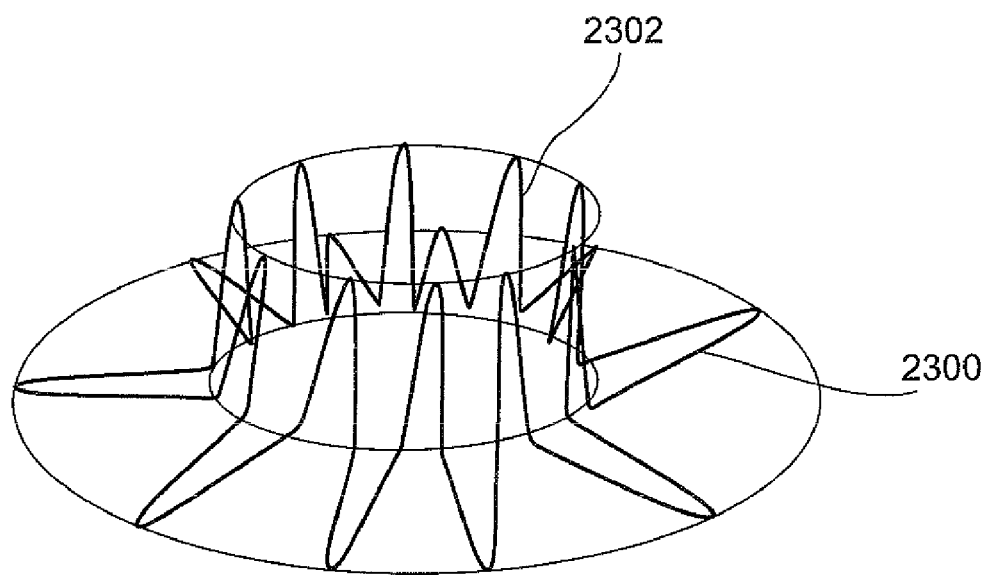
FIG. 19 is a schematic illustration of a balloon expandable branch stent graft according to an embodiment of the invention.

FIG. 19 shows another embodiment, where flaring stent portion 2300 is made in one piece with a tubular stent portion 2302.

Figure 20:
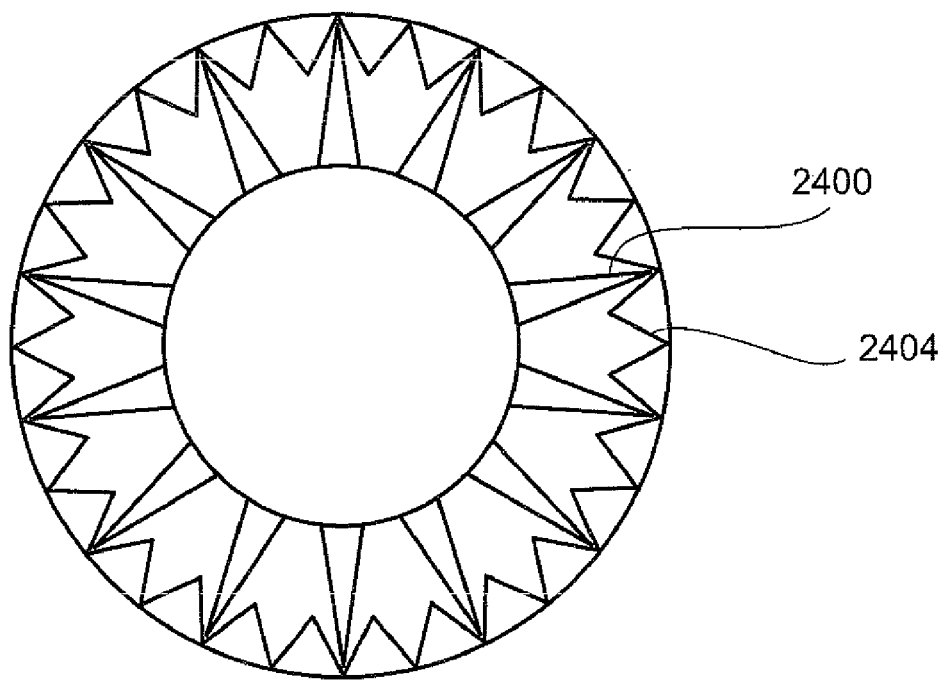
FIG. 20 is a schematic illustration of a self-expandable stent at the junction of the flaring and tubular portion of the branch stent graft according to an embodiment of the invention.

FIG. 20 shows an embodiment with a flaring stent portion 2400 made in one piece with the tubular stent portion (not shown), and in addition, a separate expanding stent 2404.

Graft portions of stent graft 2100 may be made of Dacron, polyester, polytetrafluoroethylene (PTFE) or any other bio- and hemo-compatible fabric or polymer known in the art, which is used for vascular grafts. The material used in flaring graft 2108 and in the graft of tubular portion 2106 may be the same or different.

Optionally, flaring end 2108 and the graft of tubular portion 2106 are made of one piece of fabric. Alternatively, they are formed of two pieces connected together, for instance, by suture.

Optionally, in flaring portion 2108, the stent is attached to the luminal surface of the graft so it does not intervene between the fabric of the branch stent graft and that of the aortic stent graft.

Optionally, the stent of tubular portion 2106 and stent 2108', expanding flaring end 2108, are physically connected (as shown in FIG. 19); alternatively they are separate (as shown in FIG. 18A). Optionally, they are of the same type (balloon expandable or self-expandable); alternatively they are each of a different type. In the embodiment of FIG. 18A, they are both self-expandable. Optionally, the stent type may change from balloon expandable to self-expandable along the tubular portion of the stent graft. For example, the flaring portion and the tubular region near it may be balloon-expandable and the rest of the tubular portion may be self expanding. This embodiment may result in a stronger, less flexible, flaring portion.

Figure 21:
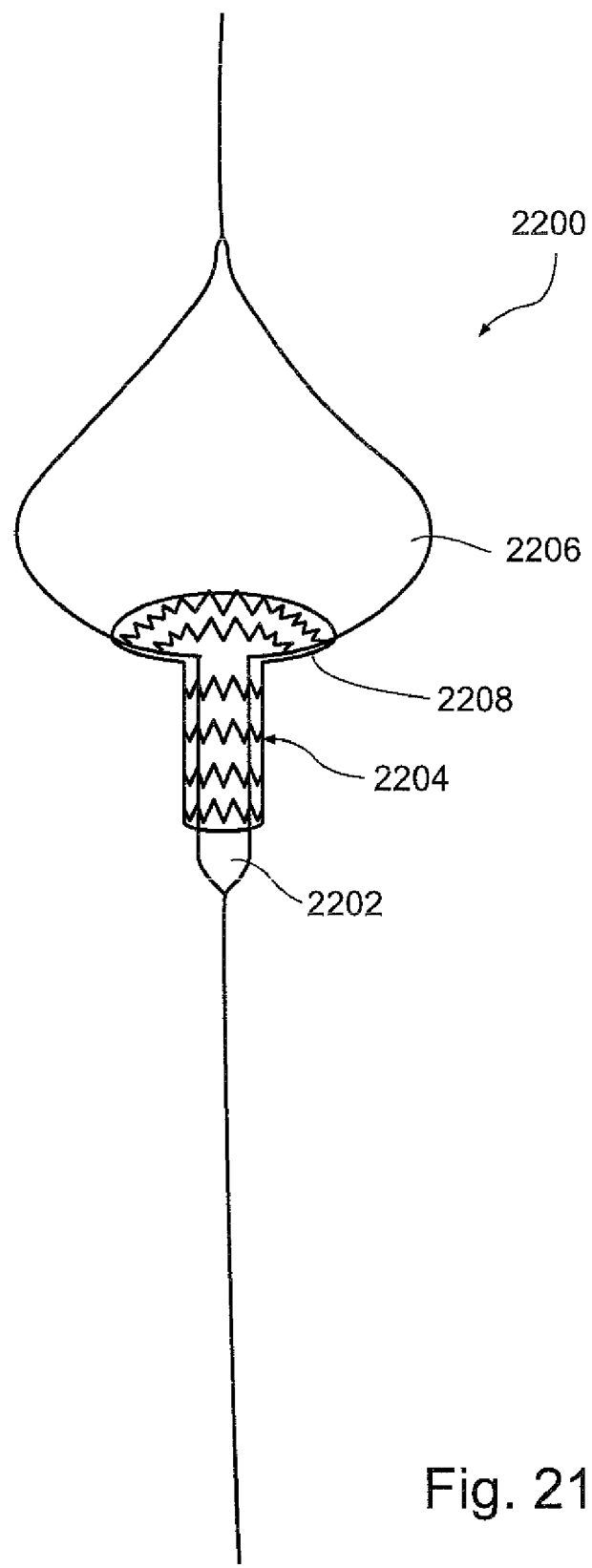
FIG. 21 is a schematic illustration of a balloon expandable branch stent graft with a flaring portion having an additional stent at the periphery of the flaring portion according to an embodiment of the invention.

FIG. 21 shows a branch stent graft 2200 according to an embodiment of the invention; where both the flaring portion and the tubular portion are balloon expandable. Optionally, the balloon or balloon portion 2202 made to expand the tubular portion 2204 of the side-branch is designed to exactly fit into the blood vessel (not shown) of the specific patient, because a balloon that is too broad might explode the branching blood vessel. On the other hand, a balloon or balloon portion 2206 for expanding the flared portion 2208 requires less accurate fitting to the dimensions of each patient. Preferably, the diameter of the tubular portion will be chosen to fit the branch artery treated.

Optionally, stent graft 2100 has a rotational radio-opaque marker (such as a gold marker) on one or both of the flaring end of the graft and the tubular portion. This may be of particular advantage in embodiments where the stent graft does not have radial symmetry, for instance, in case the flared portion is eccentric or scalloped to accommodate anatomic variability and avoid covering of nearby orifices.

A Stent Graft with Stabilizing Wires

Figure 22:
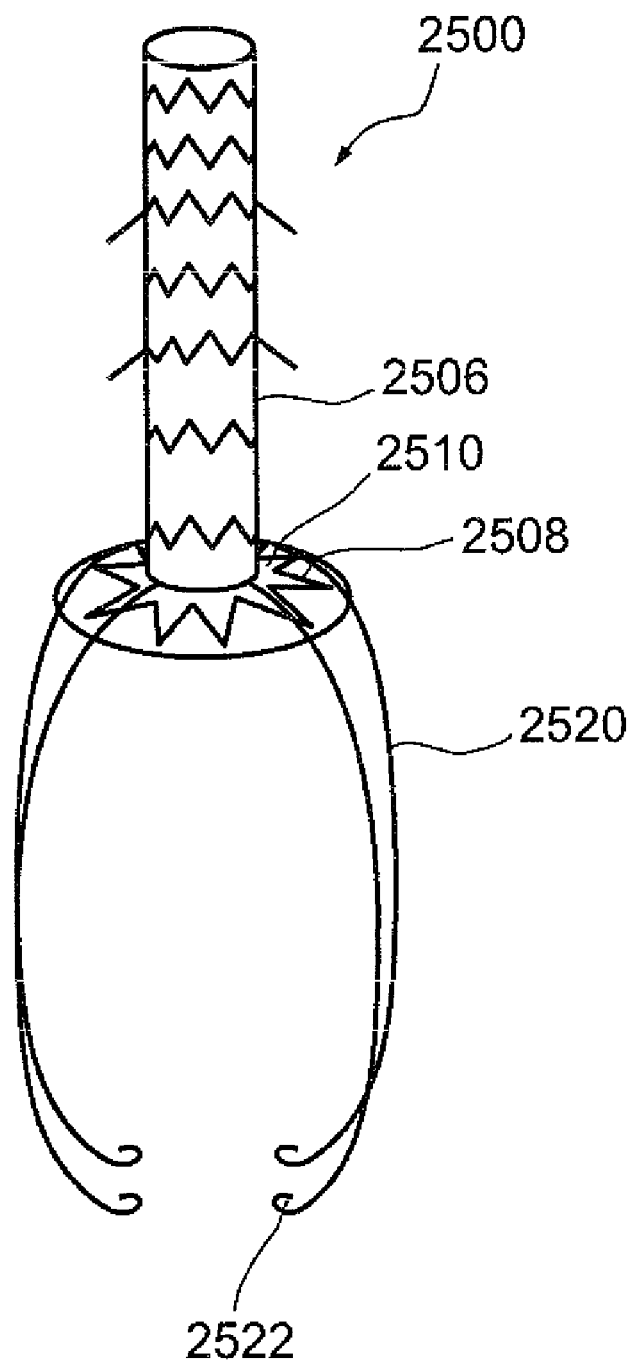
FIG. 22 is a schematic illustration of a branch stent graft with stabilizing wires according to an embodiment of the invention.

FIG. 22 is a schematic illustration of a branch stent graft 2500, according to another exemplary embodiment of the invention. Stent graft 2500 has a flaring graft end 2508 and an expanding stent-portion 2510 supporting end 2508, similar to parts 2108 and 2108' of FIG. 18A. In addition, attached to the flaring end 2508 and flaring stent portion 2510, branch stent graft 2500 has stabilizers 2520, configured for fixing the flared portions of the branch stent graft within the aortic stent graft as illustrated in FIG. 27C.

In the embodiment shown, stabilizers 2520 are curved wires, optionally made of nitinol, each having a looped tip 2522 for pressing against the aortic graft opposite of the fenestration. Stabilizers 2520 extend from the tubular stent graft 2506 graft along the flared portions 2508 and 2510 and measure from about 25 mm and up to about 100 mm.

Figure 23:
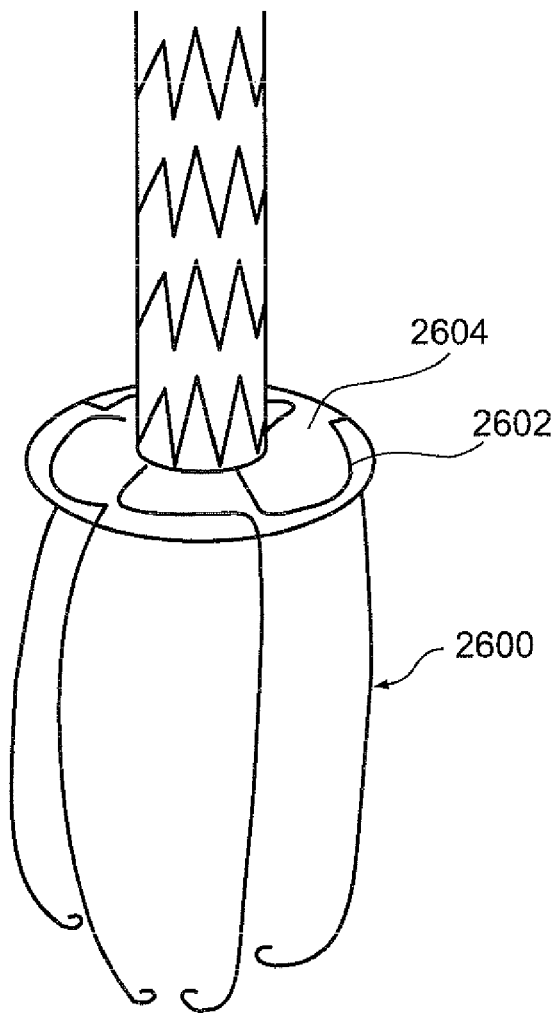
FIG. 23 is a schematic illustration of a branch stent graft with stabilizing wires according to another embodiment of the invention.

FIG. 23 schematically illustrates stabilizer wires according to another embodiment of the invention. In the embodiment illustrated in FIG. 23, stabilizers 2600 run a short circular course 2602 close to the edge of the flared graft potion (2604) before extending outwards into the aortic stent graft (not shown).

Once released inside an aortic stent graft, stabilizers 2520 push the flared portion against the aortic stent graft (FIG. 27C) in the peri-fenestration area and fix the two grafts together, aiding in achieving a seal.

A Stent Graft with Inflatable Cuffs

Figure 24:
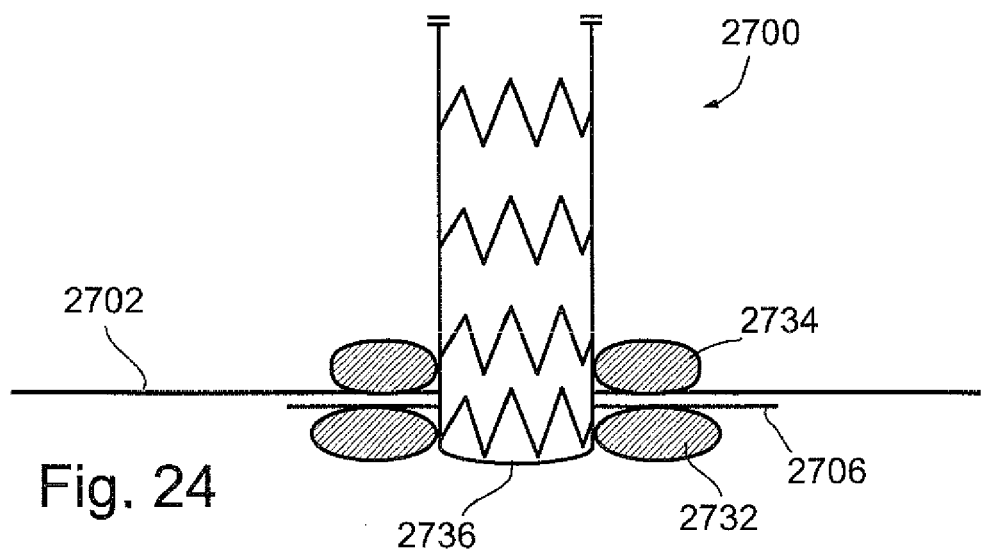
FIG. 24 is a schematic illustration of a branch stent graft with sealing cuffs according to an embodiment of the invention.

FIG. 24 schematically illustrates a branch stent graft 2700 according to an embodiment of the invention, shown in a lateral view. Branch stent graft 2700 has a proximal portion equipped with 2 circumferential inflatable cuffs 2732, 2734. Each of cuffs 2732 and 2734 has an inflating tube (not shown), accessible from outside the patient. Preferably, the cuffs are inflated by a fluid that solidifies with time at body temperature, such as blood or polymers such as cyanoacrylate resin, and 2-hydroxymethyl methacrylate (HEMA). Optionally, the inflating tubes are removable, such that after the fluid solidifies and no further inflating is required, they may be disconnected from the cuff.

In the embodiment shown, cuffs 2732 and 2734 are placed sufficiently close to each other, so that when inflated they press against each other with the fabric of aortic stent graft 2702 compressed between them. This embodiment is optionally used in cases where the aneurysm to be treated creates large enough a distance between the fenestration in the aortic stent graft and the branch orifice.

In an exemplary embodiment of the invention, the cuffs have non-circular cross-section in a plane parallel to the axis of the branch stent graft, for instance, the cuffs may have an oval cross-section, as shown in FIG. 24. Optionally, proximal cuff 2732 is positioned close to tip 2736 of the branch stent graft 2700, and the stent graft extends into the aortic stent graft several mm beyond cuff 2732.

In an embodiment of the invention, inflatable cuffs are used as a sole sealing mechanism. Alternatively, inflatable cuffs are used together with other sealing mechanism(s), for instance, with a flaring end as discussed in the context of FIG. 18A.

In an exemplary embodiment of the invention, branch stent graft 2700 has a flaring end 2706 arising from between cuffs 2732 and 2734, rather than being connected to the end of the tubular portion of the branch stent graft as in the embodiment shown in FIG. 18A.

In another exemplary embodiment of the invention, the branch stent graft is equipped with only one inflatable cuff, located distal to a flaring end of the branch graft, as to be inflated outside the aortic stent graft while the flared portion is inside it.

Exemplary Delivery Systems

Figure 25:
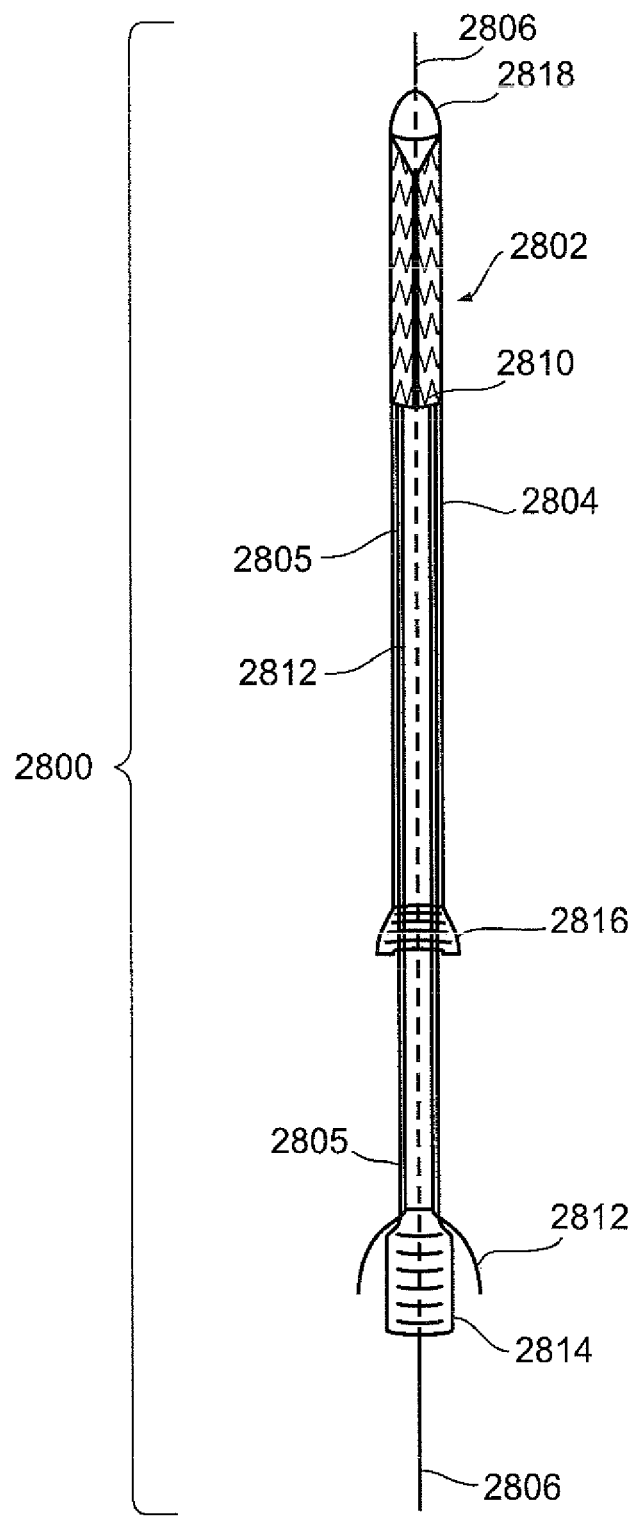
FIG. 25 is a schematic illustration of a delivery system loaded with a branch stent graft according to an embodiment of the invention.

FIG. 25 schematically illustrates an exemplary delivery system 2800 loaded with a branch stent graft according to an embodiment of the invention. Delivery system 2800 carries a branch stent graft 2802 in a compressed form within a sheath 2804. Optionally, sheath 2804 has an outer diameter of from about 12F to about 18F.

Branch stent graft 2802 is optionally a completely self expanding stent system, and its delivery is achieved by retraction of sheath 2804 backwards over a central rod 2805, so that stent graft 2802 is exposed and allowed to expand.

Delivery system 2800 is an over-the-wire system, and the wire (2806) is optionally of outer diameter between 0.035" and 0.038". A flushing port (not shown) optionally communicates with the wire lumen for fluid priming and flushing.

Delivery system 2800 is short, and has a length of from about 30 cm to about 80 cm altogether (i.e. including the handle, 2814).

Delivery system 2800 is equipped with a mechanism for preventing branch stent graft 2802 from releasing inadvertently from sheath 2804. This may be advantageous when system 2800 is used for deploying the branch stent graft in a method comprising pulling the branch stent graft, such as the methods described below under the heading "deployment methods".

Inadvertent release is prevented in delivery system 2800 with string 2812. Optionally, string 2812 is a suture, or any other kind of wire that is strong enough to prevent inadvertent release of the stent graft from the delivery system when the stent graft is pulled.

Back end 2810 of branch stent graft 2802 is fixed to central rod 2805 by string 2812 that runs through it inside central rod 2805 and reaches handle 2814. The catheter tip, 2818 is relatively short to facilitate a 90° entry from the branch artery to the aorta, and deployment into the aortic stent graft.

In operation, the back end 2816 of sheath 2804 is pulled back towards the handle (2814), releasing branch stent graft 2802. When the flared portion is expanded, the entire system 2800 is pulled back to appose the expanded flaring portion against the fenestration. Subsequently, the sheath is pulled back further to release the tubular portion, and when this is complete, string 2812 is cut.

An Alternative Mechanism for Preventing Inadvertent Release

Figure 26A:
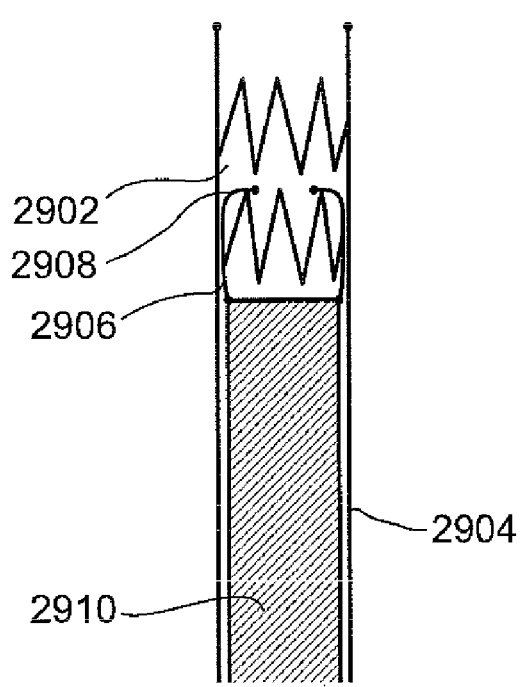
FIGS. 26A and 26B are schematic illustration of a mechanism for fixing a branch stent graft to the delivery system according to an embodiment of the invention.
Figure 26B:
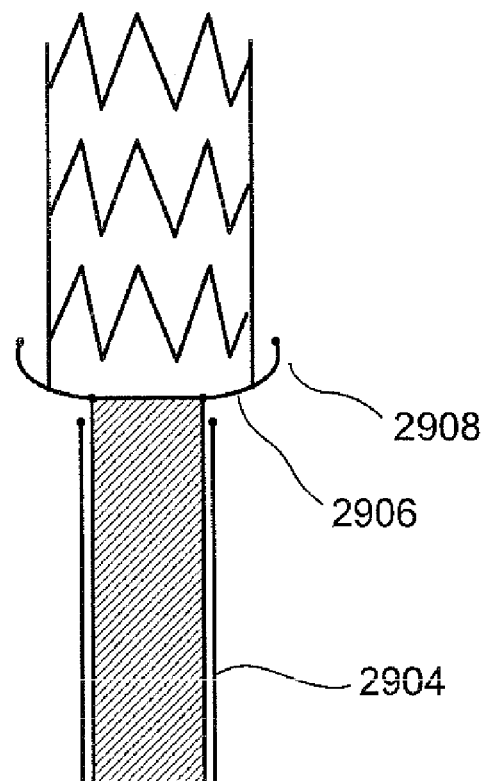

FIGS. 26A and 26B schematically illustrate a portion of a delivery system having an alternative mechanism for preventing inadvertent release. FIG. 26A shows a branch stent graft 2902 provided in a compressed form within a sheath 2904, and held compressed against a central rod 2910. Branch stent graft 2902 is compressed by metal hooks 2906, having tips 2908 compressed into the rear end of stent graft 2902 by sheath 2904. FIG. 26B shows that when outer sheath 2904 is fully withdrawn, that is, at the end of the deployment, hooks 2906 open to release the stent graft.

Delivering a Branch Stent Craft having Wire Stabilizers

Figure 27A:
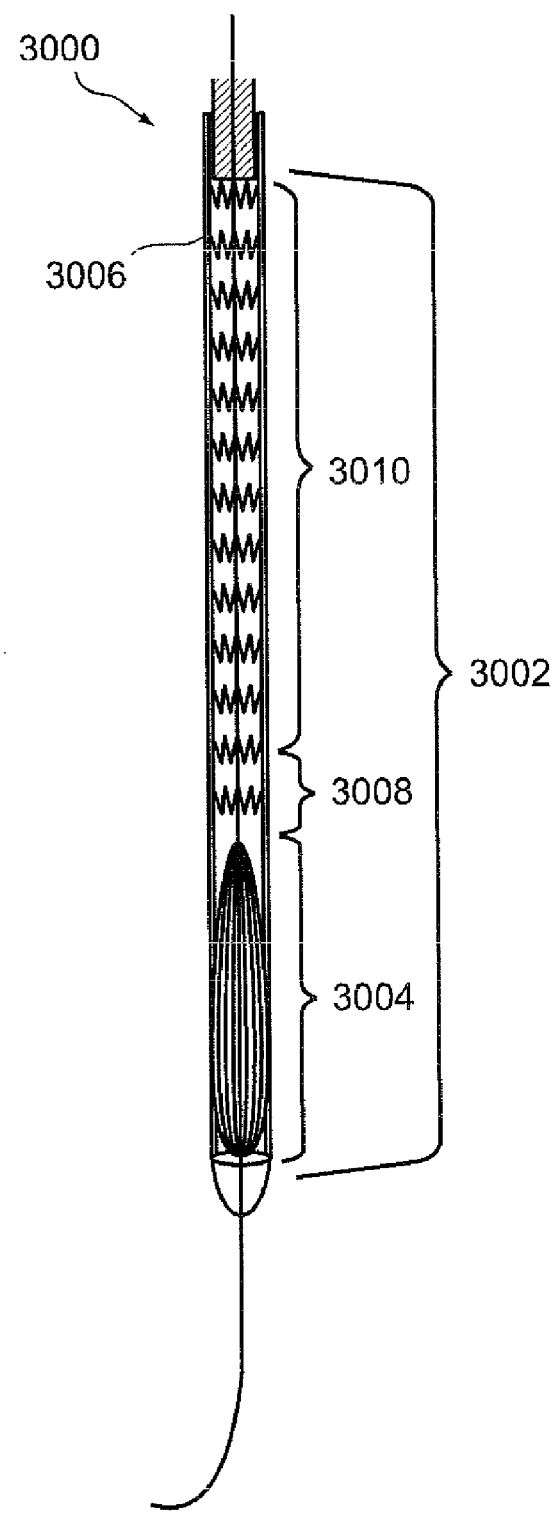
FIG. 27A is a schematic illustration of a delivery system for delivering a branch stent graft with stabilizing wires according to an embodiment of the invention.
Figure 27B:
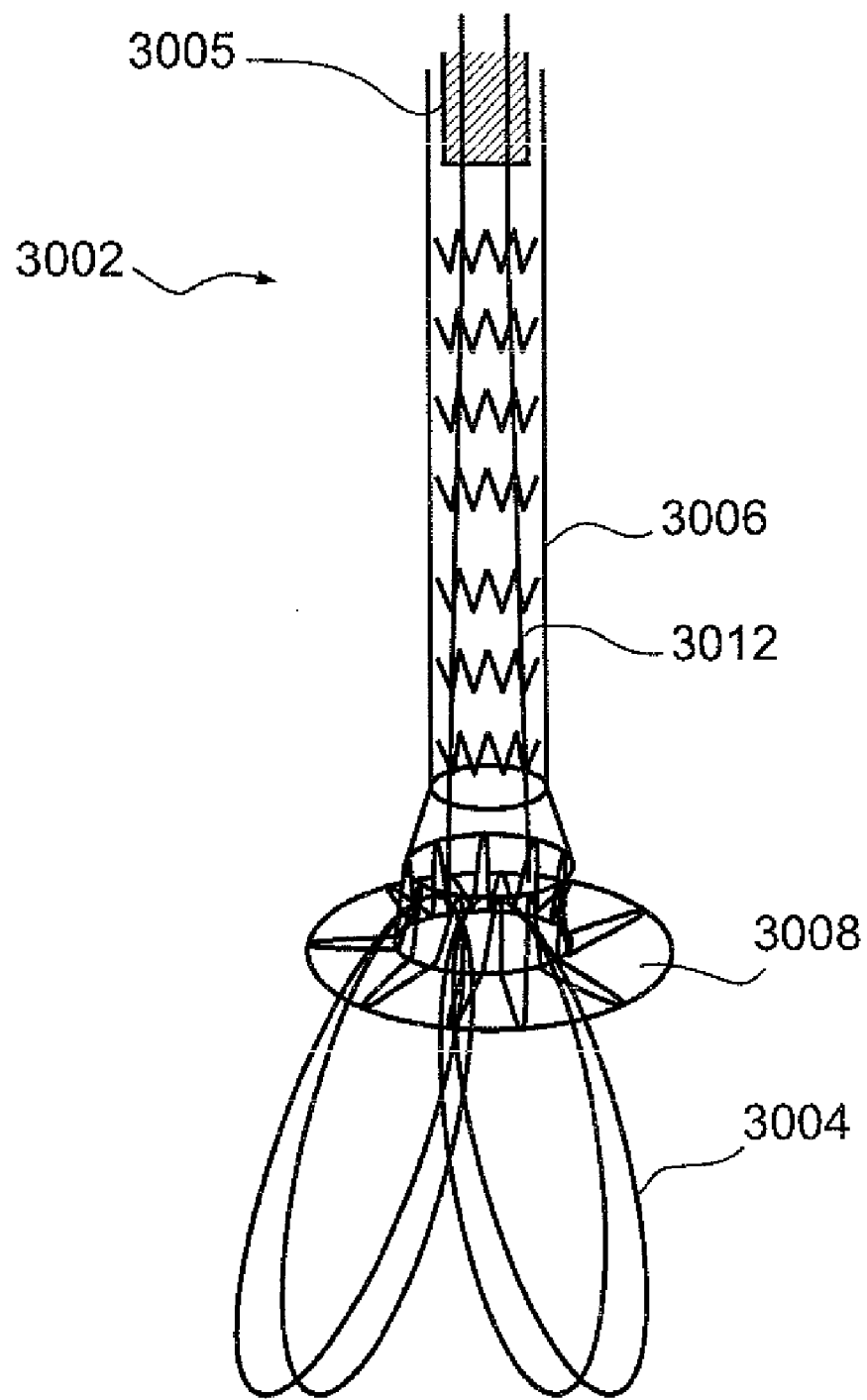
FIG. 27B is a schematic illustration of a branch stent graft with stabilizing wires after the deployment sheath has been partially withdrawn.
Figure 27C:
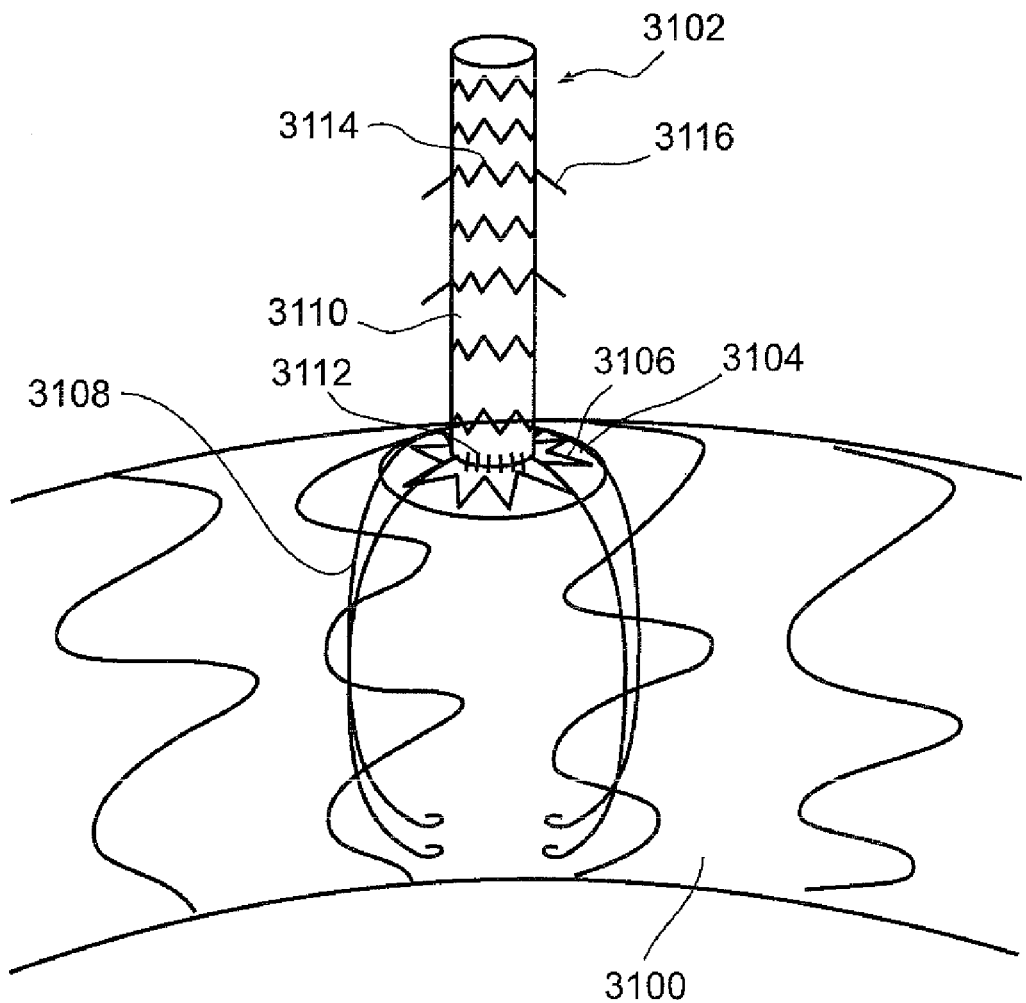
FIG. 27C is a schematic illustration of a branch stent graft with stabilizing wires deployed with an aortic stent graft according to an embodiment of the invention.

FIGS. 27A-27C schematically illustrate delivery of a branch stent graft having wire stabilizers.

FIG. 27A shows the branch stent graft within a delivery system 3000. The branch stent graft (3002) has wire stabilizers 3004, folded over within deployment sheath 3006 of delivery system 3000. The branch stent graft is also shown to have a flaring portion 3008 and a tubular portion 3010. In the figure, the wire stabilizers are folded twofold, but all degrees of folding, for instance, fourfold, are also in accordance with embodiments of the invention.

FIG. 27B schematically illustrates stent graft 3002 after deployment sheath 3006 has been withdrawn from stabilizers 3004, flaring portion 3008, and the tubular portion adjacent thereto. Flaring portion 3008 is shown fully expanded and stabilizers 3004 still folded. Stabilizers 3004 are kept folded with the aid of a suture. Suture 3012 holds in place tips 2522 (shown in FIG. 22) of the stabilizers and runs through the delivery sheath 3006 to the deployment handle (not shown) along central rod 3005. Once flaring portion 3008 is fully deployed, stabilizing wires 3004 may be released into the aortic stent graft with subsequent full deployment of the tubular portion of the branch stent graft, as illustrated in FIG. 27C.

In another embodiment of the invention, stabilizing wires 3004 are released at a later stage, for instance, after the tubular portion of the branch stent graft is released from the delivery sheath.

FIG. 27C schematically shows an aortic stent graft 3100, with a fully deployed branch stent graft 3102 according to an embodiment of the invention. The graft of the aortic stent graft has an opening, to which the branch stent graft is sealed. Reliable sealing is aided with a flaring graft portion 3104 attached to a graft portion of aortic stent graft 3100 with a flaring stent portion 3106 and stabilizing wires 3108 that press against the opposite wall of the aortic stent graft to fix the flared stent portion against the luminal surface of the aortic stent graft.

A tubular graft portion (3110) is sutured to the flaring graft portion (3104) with a suture (3112).

A tubular stent portion (3114) of branch stent graft 3102 is optionally physically separate from the flaring stent portion (3106). Tubular stent-portion 3114 is connected to metal, optionally nitinol, hooks or barbs (3116) configured to prevent movement of the tubular portion of the branch stent graft inside the blood vessel, in which stent graft 3102 is to be deployed.

An Exemplary Deployment Method

Figure 28:
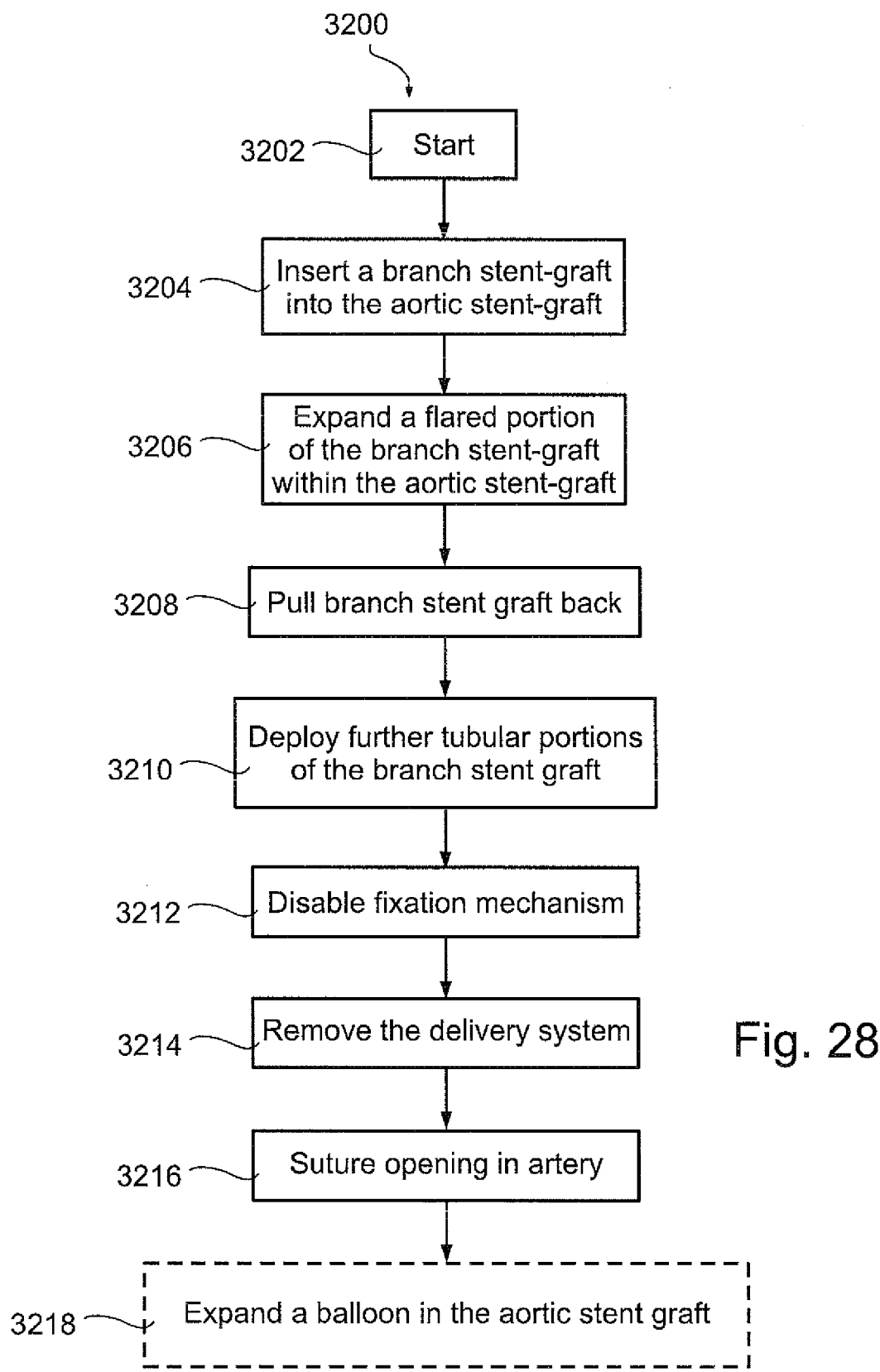
FIG. 28 is a flowchart showing actions performed during deployment of a branch stent graft according to an embodiment of the invention.

FIG. 28 is a flowchart showing actions taken in a method (3200) of deploying a branch stent graft in accordance with an embodiment of the invention. FIGS. 29-33 schematically illustrate an aorta with aortic stent graft at different stages of executing the method described in FIG. 28.

At 3202, the procedure starts when an aortic stent graft (3302 in FIGS. 29A, 29B) having an opening (3304) is positioned in the aorta (3306). The aortic graft (3302) may be fully deployed (as illustrated in FIG. 29A) or partially deployed (FIG. 29B).

Positioning aortic stent graft 3302 and creating opening 3304 may be in accordance with a state of the art method.

Figure 29A:
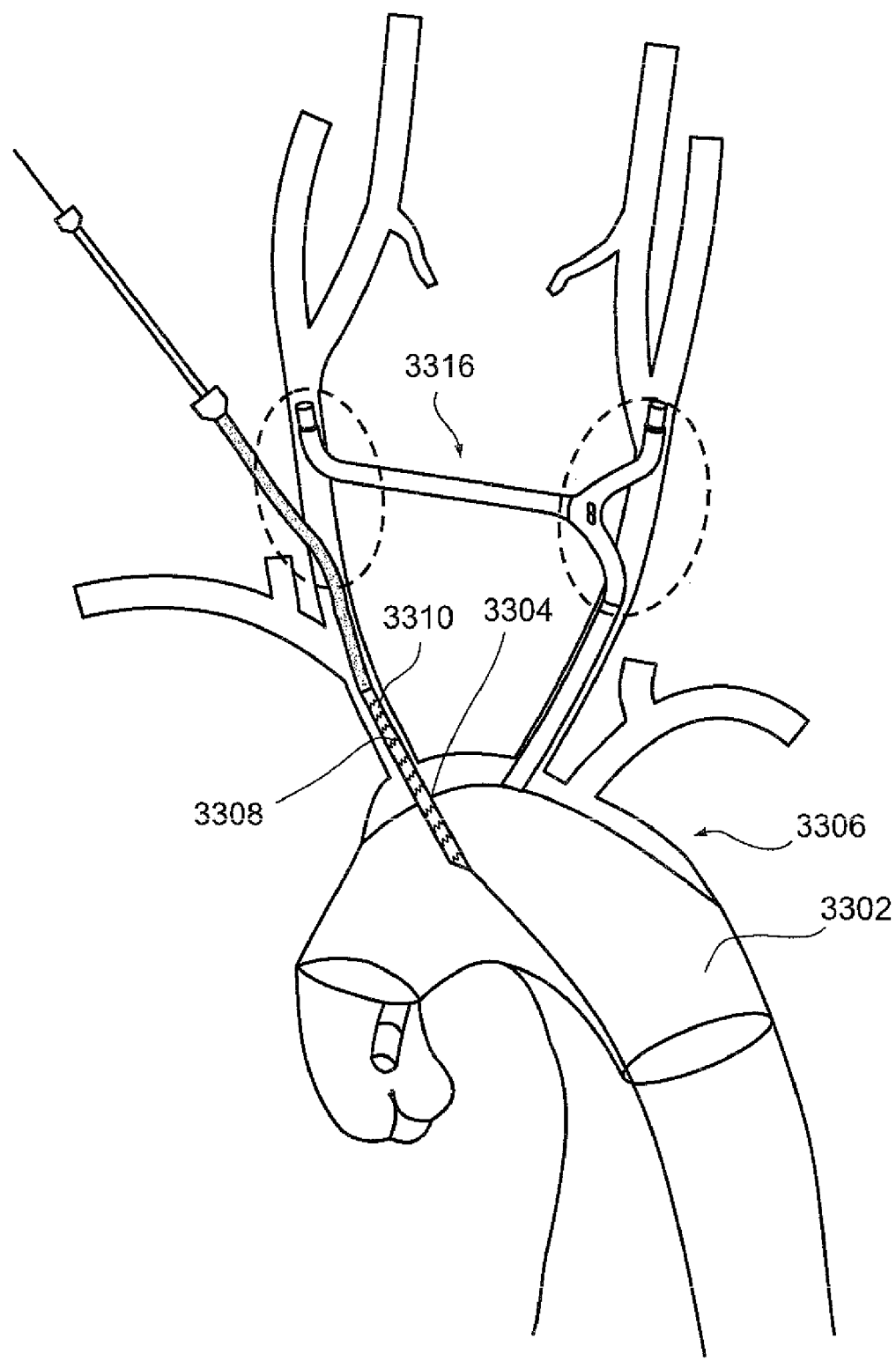
FIGS. 29A and 29B are schematic illustrations of an aorta during deployment of a branch stent graft according to two embodiments of the invention.
Figure 29B:
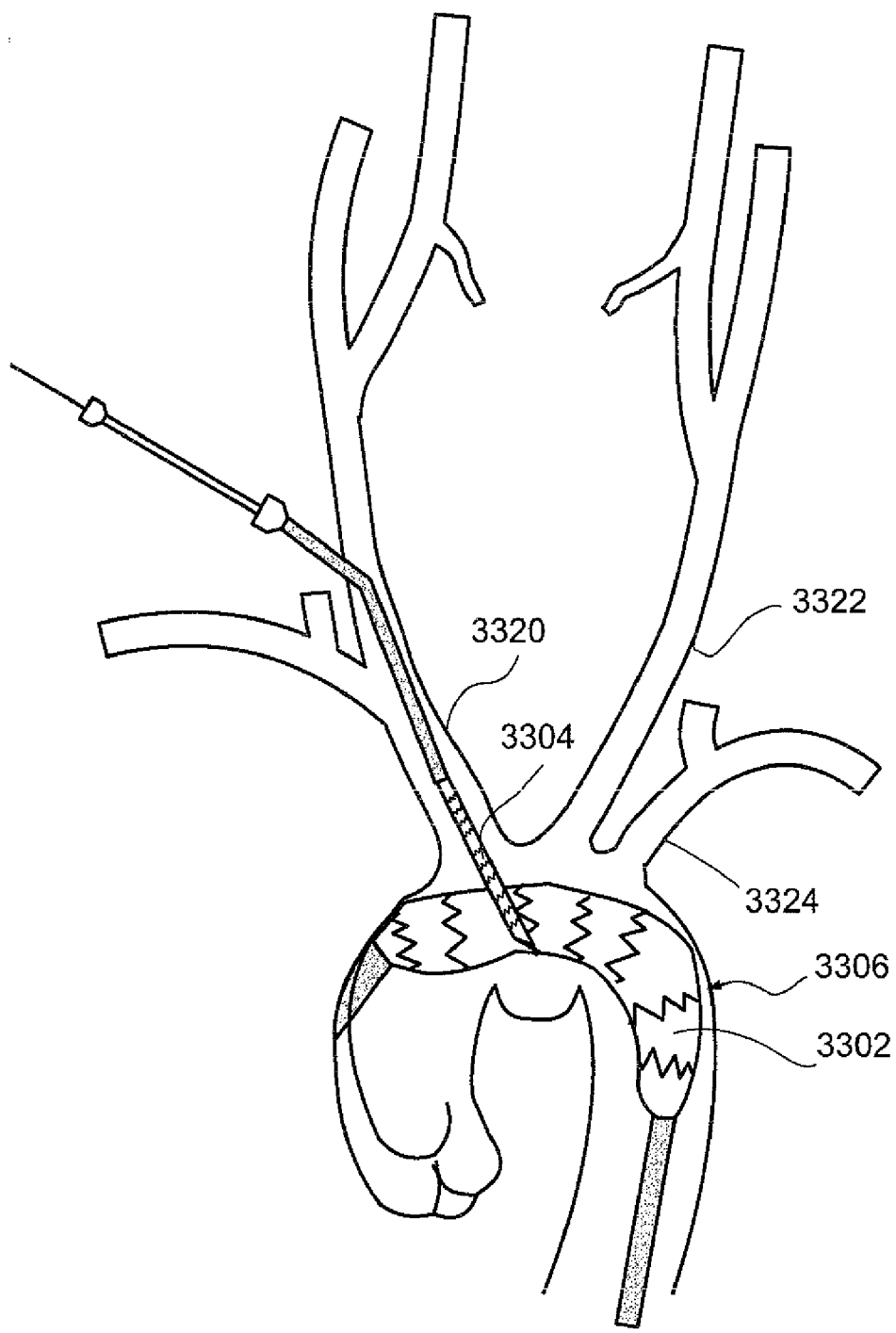
Figure 30:
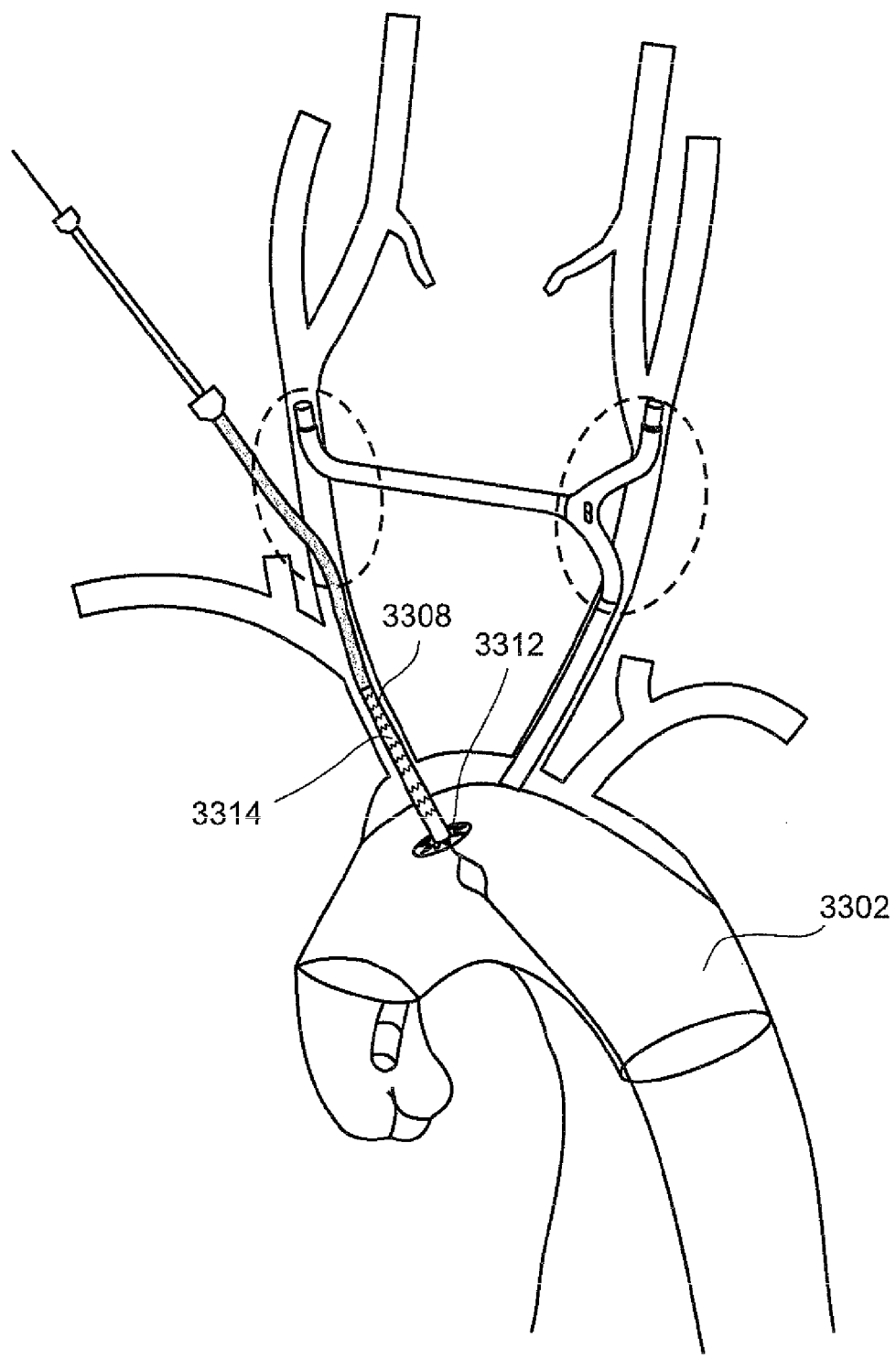
FIGS. 30-33 are schematic illustrations of an aorta during various stages of deployment of a branch stent graft according to an embodiment of the invention.
Figure 31:
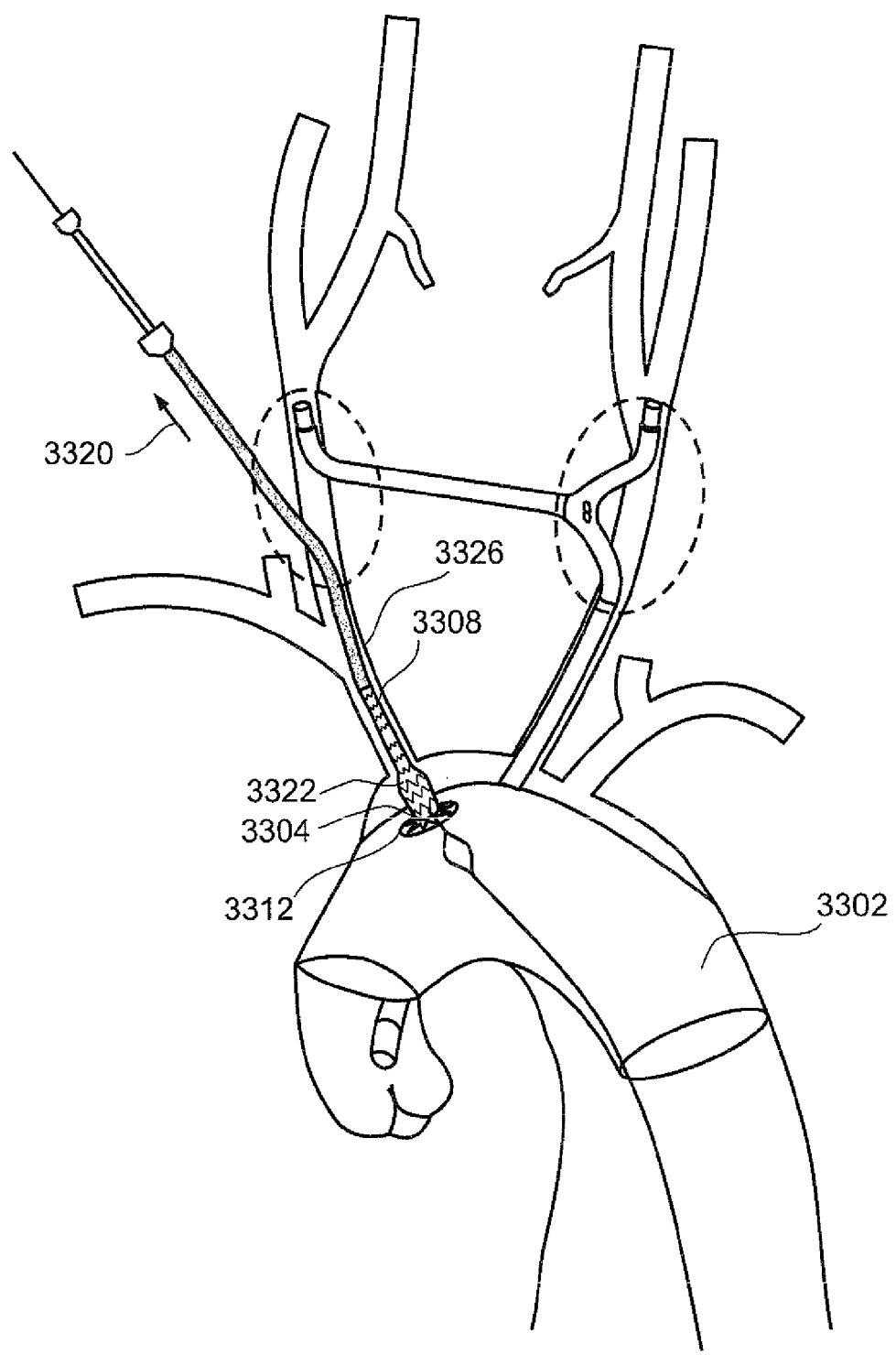
Figure 32:
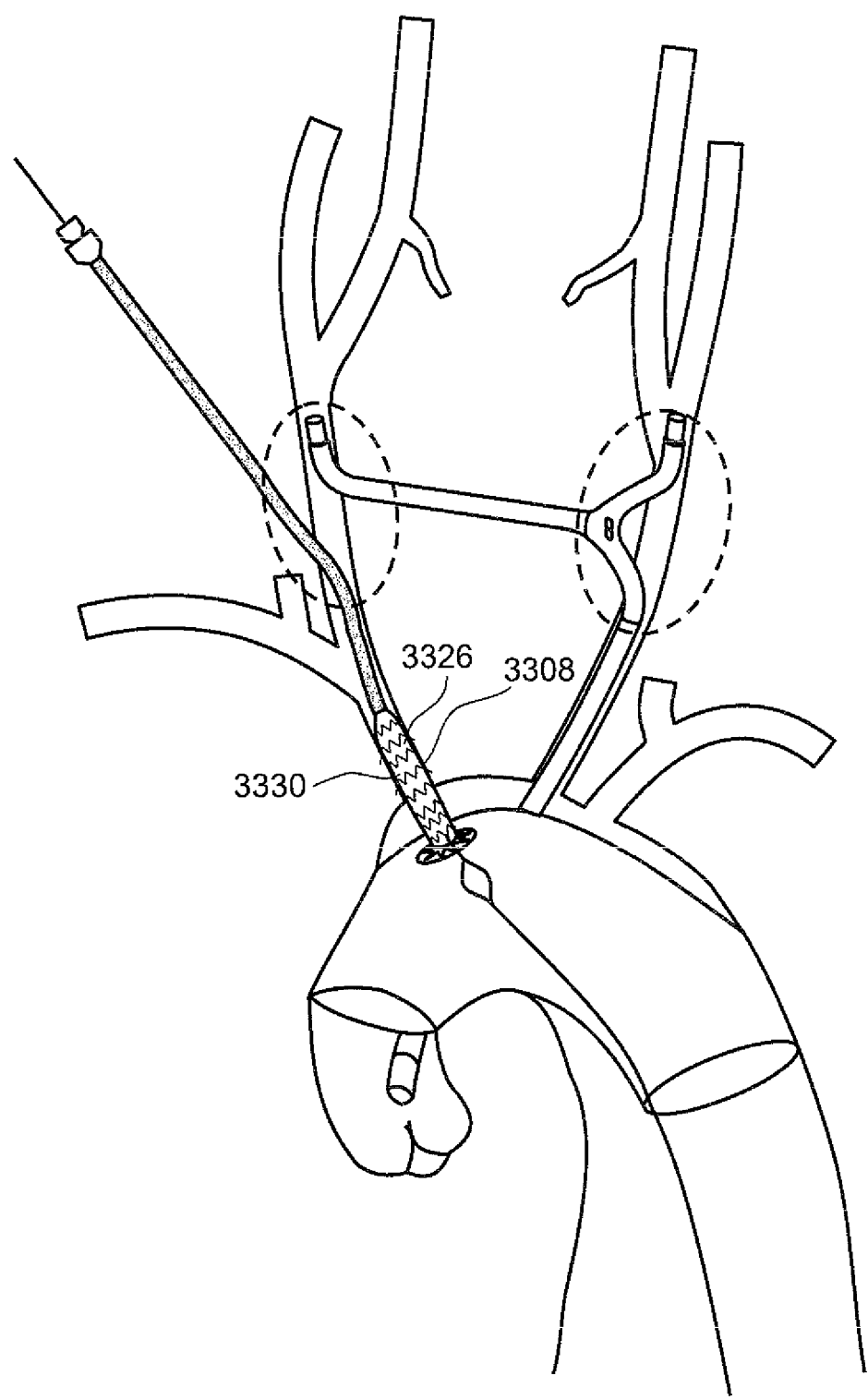

Optionally, in the embodiment shown in FIG. 29A, the aortic stent graft is deployed and fenestrated in accordance with one of the embodiments described above, in relation to FIGS. 1 to 17. Optionally, in the embodiment of FIG. 29B, the aortic stent graft is fenestrated and the branch stent graft connected to the aortic stent graft while the aortic stent graft is only partially expanded in its radial direction. This way, the brain supplying blood vessels 3320, 3322, 3324, branching from the aortic arch are not occluded, and the bypass 3316 (FIG. 29A) may be omitted.

At 3204, a self expanding branch stent graft (3308) is inserted into aortic stent graft 3302 through opening 3304.

At 3206, A flared portion 3312 (shown in FIG. 30) of stent graft 3308 is expanded within aortic stent graft 3302, by pulling backwards deployment sheath 3310.

At 3208, branch stent graft 3308 is pulled back in the direction of arrow 3320 (see FIG. 31) as to appose flared portion 3312 of the branch stent graft to the luminal surface of aortic graft 3302 at opening 3304. At the same time, a tubular portion 3322 of branch stent graft 3308 is expanded as to start deployment of the branch stent graft in the innominate artery 3326.

3208 is a stage where fixing stent graft 3308 to the delivery system, as discussed, for instance, in the context of FIGS. 25 and 26, is of particular importance, as this is the stage where the stent graft might escape from the delivery system non-intentionally.

At 3210 (FIG. 28), the delivery sheath is further pulled backwards to let further portions of branch stent graft 3308 deploy in artery 3326 (FIG. 32), so that barbs 3330 (FIG. 32) catch in the artery wall and maintain the branch stent graft in place.

At 3212 the fixation mechanism is disabled to allow completing deployment of the tubular portion of stent graft 3308. In the embodiment of FIG. 25 disabling the fixation mechanism comprises cutting the fixation suture. In the embodiment of FIGS. 26A and 26B, disabling the fixation mechanism comprises releasing the hook (2906).

At 3214, the delivery system is removed.

Figure 33:
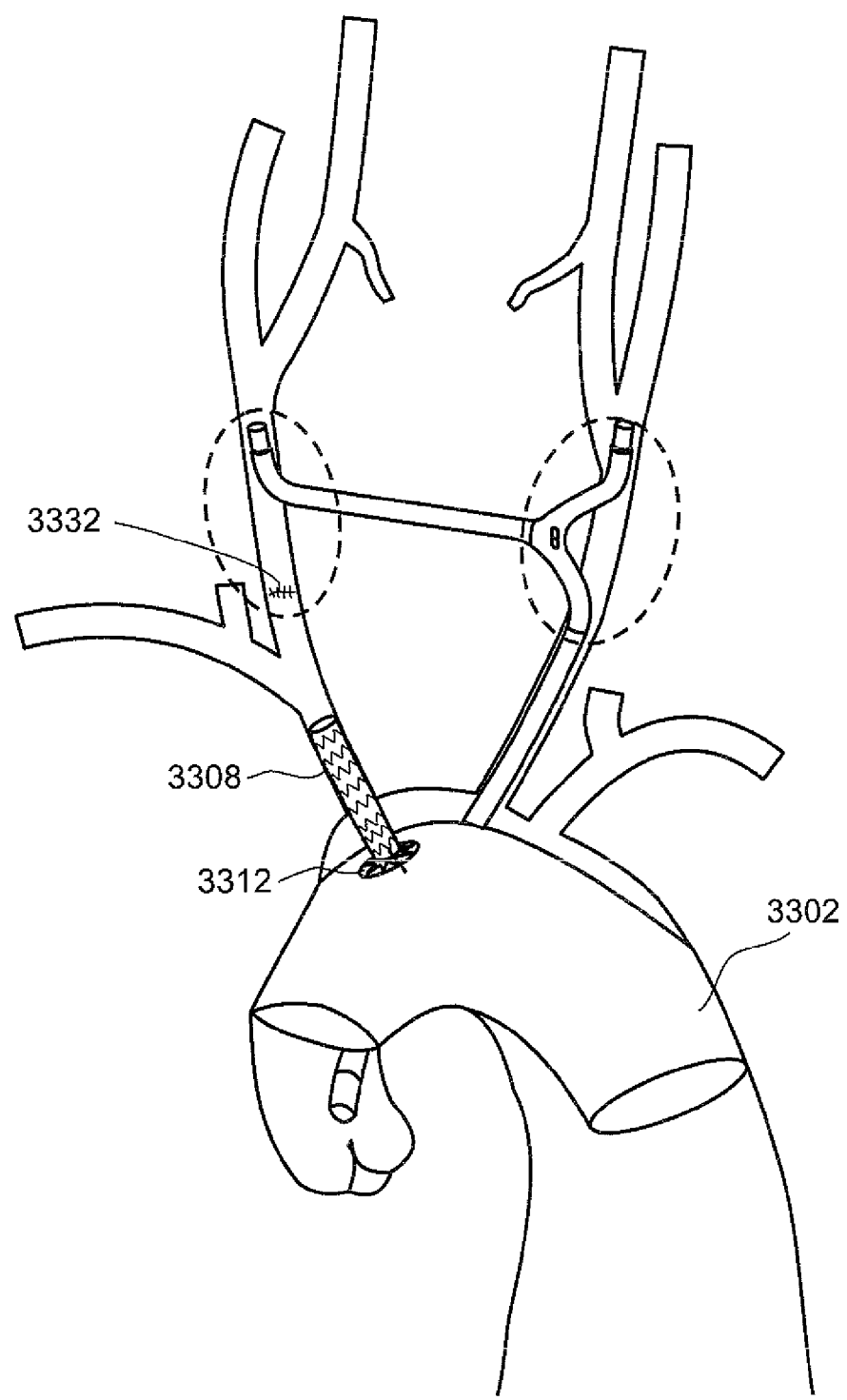

At 3216, opening 3332 in the artery, through which stent graft 3308 was delivered, is sutured (FIG. 33).

Optionally, the method includes action 3218, at which a large balloon inserted from the femoral artery is inflated in the aortic stent graft to compress flared portion 3312 of branch stent graft 3308 against the luminal surface of aortic stent graft 3302.

In an exemplary embodiment of the invention, a stent graft having an inflatable cuff as a flaring portion (see FIG. 24) is deployed in a similar method. In this method, at 3206, the proximal cuff 2732 is inflated, and at 3208, the distal cuff (if exists) is inflated.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the disclosure and/or claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents, which perform the same function, even if the structure or acts are different, as known in the art. Therefore, the scope of the invention is limited only by the elements and limitations as used in the claims.

The invention claimed is:

1. A method for deploying a stent-graft in the aorta, the method comprising
(a) positioning a shunt so that it extends inside a portion of a brain-supplying artery (BSA) and into the aorta;
(b) deploying a stent-graft in the aorta along a portion of the shunt, wherein deploying the stent graft comprises forming in the stent graft an opening facing a BSA or aligning an opening in the stent graft to face a BSA; and
(c) removing the shunt.

2. The method according to claim 1, wherein deploying the stent-graft comprises forming in the stent-graft an opening facing a BSA.

3. The method according to claim 1, wherein deploying the stent-graft comprises aligning an opening in the stent-graft to face a BSA.

4. The method according to claim 1, wherein deploying the stent-graft comprises positioning a side-branch of the stent-graft in one or more of the BSAs, such that the side-branch is connected to the stent-graft at the vicinity of an opening in the stent-graft, the opening facing the BSA.

5. The method according to claim 4, wherein the stent-graft comprises a side-branch, and positioning a side-branch of the stent-graft in a BSA comprises extending said side-branch into the BSA.

6. The method according to claim 4, wherein positioning a side-branch in a BSA comprises preparing the side-branch in situ.

7. The method according to claim 6, wherein positioning a side-branch in a BSA comprises insertion of a side-branch from a femoral artery through the stent-graft and an opening in the stent-graft, said opening facing said BSA.

8. The method according to claim 6, wherein positioning a side-branch in a BSA comprises insertion of a side-branch from the BSA into an opening in the stent-graft, and dilating a portion of the side-branch to hold the stent-graft from the inside of the stent-graft.

9. The method according to claim 1, further comprising holding the stent-graft in place to prevent its dislodging during removal of the shunt.

10. The method according to claim 9, wherein holding the stent-graft in place comprises inflating a balloon inside the stent-graft.

11. The method according to claim 9, wherein holding the stent-graft in place comprises momentarily stopping the heart.

12. The method according to claim 1, wherein the brain-supplying artery is one of the following: the left subclavian artery; the left common carotid artery, the right common carotid artery and the innominate artery.

13. The method according to claim 1, wherein removing the shunt comprises expanding an expandable device between the stent-graft and the aorta to facilitate release of the shunt.

14. The method according to claim 13, wherein the expandable device is a balloon.

15. The method according to claim 1, wherein the shunt comprises a stiff segment and a sleeve going around and along the stiff segment, and removing the shunt comprises inverting the sleeve.

16. The method according to claim 1, further comprising connecting the brain-supplying artery to a second brain-supplying artery with a carotid perfusion catheter, such that if the passage between the aorta and the second brain-supplying artery is occluded, blood flows into the second brain-supplying artery through the carotid perfusion catheter.

17. The method according to claim 16, further comprising insertion of a fenestration instrument through the second BSA and forming an opening in the stent-graft, the opening facing the second BSA.

18. The method according to claim 1, wherein after the shunt is removed from the brain-supplying artery a fenestration instrument is inserted through the brain-supplying artery and an opening is formed in the stent-graft, the opening facing the brain-supplying artery.

* * * * *